US011732012B2

(12) United States Patent
Qin et al.

(10) Patent No.: US 11,732,012 B2
(45) Date of Patent: Aug. 22, 2023

(54) ATTENUATED STRAINS OF ONCOLYTIC RHABDOVIRUS AND USES THEREOF IN TUMOR TREATMENT

(71) Applicant: HANGZHOU EVERBRIGHT BIOLOGICS, LTD., Zhejiang (CN)

(72) Inventors: Frank XiaoFeng Qin, Jiangsu (CN); Jing Xia, Jiangsu (CN)

(73) Assignee: FANTASIA BIOPHARMA (ZHEJIANG) CO. LTD., Zhejiang (CN)

(*) Notice: Subject to any disclaimer, the term of this patent is extended or adjusted under 35 U.S.C. 154(b) by 242 days.

(21) Appl. No.: 17/030,737

(22) Filed: Sep. 24, 2020

(65) Prior Publication Data

US 2021/0171583 A1 Jun. 10, 2021

Related U.S. Application Data

(63) Continuation of application No. PCT/CN2018/080699, filed on Mar. 27, 2018.

(51) Int. Cl.

| | |
|---|---|
| ***C07K 14/145*** | (2006.01) |
| ***A61K 39/205*** | (2006.01) |
| ***A61P 35/00*** | (2006.01) |
| ***A61K 45/06*** | (2006.01) |
| *A61K 38/00* | (2006.01) |
| *A61K 39/00* | (2006.01) |

(52) U.S. Cl.

CPC .......... *C07K 14/145* (2013.01); *A61K 39/205* (2013.01); *A61K 45/06* (2013.01); *A61P 35/00* (2018.01); *A61K 38/00* (2013.01); *A61K 2039/525* (2013.01)

(58) Field of Classification Search

None

See application file for complete search history.

(56) References Cited

U.S. PATENT DOCUMENTS

| | | | | |
|---|---|---|---|---|
| 2007/0098743 A1* | 5/2007 | Bell | C12N 7/00 435/235.1 |
| 2014/0370043 A1* | 12/2014 | Kang | A61P 31/14 435/235.1 |
| 2016/0144022 A1 | 5/2016 | Kang et al. | |

FOREIGN PATENT DOCUMENTS

| | | |
|---|---|---|
| WO | 2004085658 A1 | 10/2004 |
| WO | 2013091080 A1 | 6/2013 |
| WO | 2014205579 A1 | 12/2014 |

OTHER PUBLICATIONS

Sung et al. Combined VSV oncolytic virus and chemotherapy for squamous cell carcinoma. Laryngoscope. Feb. 2008;118(2):237-42.*

Hoffmann et al. ("Fusion-active glycoprotein G mediates the cytotoxicity of vesicular stomatitis virus M mutants lacking host shut-off activity" in J. Gen. Virol. (2010), 91, 2782-2793).

Kim et al. ("Matrix protein gene variants of two distinct serotypes of rVSV make effective viral vectors for prime-boost vaccination" in J. Human Virol. Retrovir. (2016), 4(1):00125, 1-11).

Van Den Pol et al. ("matrix protein [recombinant vesicular stomatitis Indiana virus rVSV-G/GFP]" in GenBank (2012), ACK77582.1; equiv. to van den Pol et al. "Highly attenuated recombinant vesicular stomatitis virus VSV-12' GFP displays Immunogenic and oncolytic activity" in J. Virol. (2013), 87(2), 1019-1034).

* cited by examiner

*Primary Examiner* — Nianxiang Zou

(74) *Attorney, Agent, or Firm* — Innovar, L.L.C.; Rick Matos

(57) ABSTRACT

Provided is a modified matrix protein of a vesicular stomatitis virus, wherein the protein has amino acid substitutions at position 21, position 51, position 111 and position 221. Further provided are an attenuated strain of the vesicular stomatitis virus producing the modified matrix protein, a composition containing the attenuated strain, and uses thereof in preparing a drug for killing abnormally proliferating cells, inducing and promoting antitumor immune response, or eliminating immunosuppression in a microenvironment of a tumor tissue.

28 Claims, 15 Drawing Sheets

Specification includes a Sequence Listing.

| Virus backbone | Success rates of virus packaging |
|---|---|
| RV-WT | +++++ |
| RV-M51R | +++++ |
| RV-M51deletion | —— |
| RV-M51R-V221F | +++++ |
| RV-M51R-L111F | +++++ |
| RV-M51R-V221F-S226R | +++++ |
| RV-M-TS-GML-mut1 | +++++ |
| RV-M-TS-GML-mut2 | +++++ |
| RV-3TS(G21E+M51R+L111F) | —— |
| RV(G21E、M51A、L111F、V221F) | +++++ |
| RV(G21E、M51A、L111F、V221A) | —— |
| RV(G21E-M51A-L111A-V221F) | —— |
| RV(G21E-M51R-L111A) | —— |
| RV(G21E-M51A-L111A) | —— |
| RV-G21E、M51A、L111F | +++++ |
| RV-G21E、M51A | +++++ |
| RV-M51A | +++++ |
| RV-G21E | +++++ |

VSVG(LLC MOI 0.002)

IFNβ(LLC MOI 0.002)

A

Body weight changes of Balb/c mice

- RV-WT
- RV-M51R
- RV-M51R-V221F-S226R
- RV-G21E-M51A-L111F-V221F
- PBS

B

Survival rate curve of Balb/c mice

- RV-WT
- RV-G21E-M51A-L111F-V221F

ATTENUATED STRAINS OF ONCOLYTIC RHABDOVIRUS AND USES THEREOF IN TUMOR TREATMENT

CROSS-REFERENCE TO EARLIER FILED APPLICATIONS

This application claims the benefit of and is a continuation of PCT/CN2018/080699, filed Mar. 27, 2018, the entire disclosure of which is hereby incorporated by reference.

INCORPORATION BY REFERENCE

In compliance with 37 CFR 1.52(e)(5), the instant application contains Sequence Listings which have been submitted in electronic format via EFS and which are hereby incorporated by reference. The sequence information contained in electronic file named HEB1CNV_SEQ_ST25.txt, size 7 KB, created on Sep. 24, 2020, and in the electronic filed named 6849-170751I.TXT, size 7 KB, created on Feb. 25, 2021, using SIPOSequenceListing 1.0, are identical, contain no new matter, and are hereby incorporated by reference in their entirety.

TECHNICAL FIELD

The present disclosure mainly relates to the field of biotechnology. To be specific, the present disclosure relates to an attenuated strain of a virus and its use in the treatment of diseases. To be more specific, the present disclosure relates to a mutant attenuated strain of oncolytic rhabdovirus, particularly VSV-MuddSummer strain and its use in the methods for treating cancer.

BACKGROUND

Currently, small molecule drugs, monoclonal antibodies and similar technologies have been developed for novel therapies for tumors; however, the cure rate is not high, and more research is required. In addition, treatment with a single drug may lead to the occurrence of drug resistance in tumor cells, therefore, there is an urgent need to develop more effective biological treatment methods. Oncolytic viruses achieve replication ability via genetic alterations. Attenuated viruses that have been highly diluted are capable of taking advantage of the activation of oncogene(s) or inactivation or defect(s) of tumor suppressor gene(s) in tumor (target) cells, selectively replicating in target cells and finally resulting in the lysis and death of tumor cells, while such attenuated viruses merely exist in a small amount or are incapable of proliferating in normal cells. A tumor therapy using such virus is referred to as oncolytic virus therapy. Oncolytic viruses not only replicate themselves in tumor cells and result in the lysis and death of cells, but also release large numbers progeny virus particles from dead cells, thereby producing a cascade effect and amplifying the cytolytic effect until the tumor cells are eliminated. Meanwhile, the lysis of tumor cells causes the tumor antigens to be released from tumor cells and thus induce systemic antitumor immune response in vivo, which may enhance the cytolytic activity of the virus. After entering a tumor cell, oncolytic viruses gradually destroy the host cell via self-replication, thereby further spreading to the surroundings and entering other tumor cells. Effective antitumor effects may be exerted by such repeated circulation.

A large number of reports have shown that many viruses may replicate in a variety of tumor cells and kill tumor cells in in-vitro experiments, such as Sendai virus (Kinoh et al, 2004), Coxackie Virus (Shafren et al, 2004), herpes simplex virus (Mineta et al, 1995), parvovirus (Abschuetz et al, 2006), adenovirus (Heise et al, 2000), poliovirus (Gromeier et al, 2000), Newcastle disease virus, measles virus (Grote et al, 2001), reovirus (Coffey et al, 1998), retrovirus (Logg et al, 2001), vaccinia virus (Timiryasova et al, 1999) and influenza virus (Bergmann et al, 2001)). In addition, it has been proved that these viruses are effective for treating tumors in tumor-bearing animal models. However, as for most live viruses, safety is an important concern, so there is still a need to develop safer and more controllable oncolytic viruses to treat cancers.

With the rapid development of molecular genetics and genetic editing technology, it is possible to conduct genetic editing in a virus at molecular level, selectively recombine DNA and introduce an in-vitro site-directed mutagenesis, or the like. The changes of phenotypic traits are observed by means such as hybridization, so as to infer the existence and changes of genetic genes. Therefore, another cognitive approach from inside to outside appears in modern genetics. That is, the fine structure of a gene is modified purposefully and precisely at certain site(s) by technologies such as site directed mutagenesis, so as to determine the direct influence of these changes on phenotypic traits.

Vesicular stomatitis virus (VSV) is a negative-strand RNA virus that infects most mammalian cells and expresses viral protein accounting for up to 60% of the total protein in the infected cells. In nature, VSV might infect swines, cattles and horses, and causes chickenpox like disease near mouth and feet. Although it has been reported that human might also get infected with VSV, VSV has not caused any serious symptoms in humans. VSV encodes five kinds of proteins, including nucleocapsid protein (N), phosphoprotein (P), matrix protein (M), surface glycoprotein (G) and RNA-dependent RNA polymerase (L). Blocking the protein synthesis in the host cell by VSV matrix protein (M) may induce the death of cells.

With the development of the genetic technology of RNA viruses, vesicular stomatitis virus-based vectors have been developed into effective therapeutic preparations. VSV viral vector is an efficient oncolytic rhabdovirus vector, with which a very wide variety of tumor cells may be lysed. According to data reports, VSV vector is almost capable of infecting and lysing all kinds of tumor cells, the oncolytic ratios of VSV vector are all 50% or more in in-vitro experiments, and VSV vector is capable of significantly prolonging the life of tumor-bearing animal models in in-vivo experiments. VSV vector has also been developed into an effective vaccine vector. VSV viral vector has been applied in the development processes of vaccines for acquired immunodeficiency syndrome virus, influenza viruses, hepatitis C virus, hepatitis B virus and the like as a vaccine vector. Therefore, vesicular stomatitis virus vector has excellent application prospects.

In the field of the gene therapy for tumors, viruses are often used as the vectors of therapeutic agents. Because of safety concerns, the replication of viruses in normal cells is generally controlled, and as a result, it is technically rather difficult to achieve an infection efficiency of 100%. Therefore, using a self-replicating virus (proliferative virus) to treat a tumor (oncolytic rhabdovirus therapy) attracts much attention and expectation. Oncolytic rhabdovirus therapy takes advantage of the self-replication of the virus to infect and directly kill the tumor cell to achieve the therapeutic purpose. In addition, oncolytic rhabdovirus therapy is different from gene therapy and mainly relies on the replication of the virus in tumor cells to produce tumor cell-killing effects. The concept of oncolytic virus therapy has long existed as wild-type strains or naturally attenuated strains were used in an attempt to treat tumor 100 years ago. With the advance of genetic engineering technology, there has been rapid progress of the research on the use of viruses in therapies which led to the development of the second generation of recombinant virus.

However, VSV-based recombinant viruses known in the prior art either have certain toxicity to normal somatic cells which results in the existence of safety risks, or have poor oncolytic effects which results in poor therapeutic effects for solid tumors. Therefore, there is still a need to develop a VSV-based recombinant oncolytic rhabdovirus having both good safety property and strong oncolytic effect.

SUMMARY

Problems to be Solved by the Disclosure

Based on the problems existing in the prior art, there is a need to provide an attenuated strain of oncolytic rhabdovirus which is capable of effectively reducing the toxicity of the virus in normal somatic cells, while ensuring high selectivity for abnormally proliferating cells with respect to normal cells and having good oncolytic effect.

Means for Solving the Problems

In one technical solution, the present disclosure relates to a modified matrix protein (M) of a recombinant oncolytic rhabdovirus, wherein an amino acid sequence encoding the modified matrix protein (M) comprises a sequence which is at least 80%, preferably at least 90%, more preferably at least 95% and most preferably at least 98% identical to an amino acid sequence as set forth in SEQ ID NO: 1; and the amino acid sequence has amino acid substitutions at position 21, position 51, position 111 and position 221 as compared with SEQ ID NO: 1.

In another technical solution, the present disclosure relates to a modified matrix protein (M), wherein the recombinant oncolytic rhabdovirus is a vesicular stomatitis virus; preferably, the recombinant oncolytic rhabdovirus is Mudd-Summer strain of vesicular stomatitis virus.

In another technical solution, the present disclosure relates to a modified matrix protein (M), wherein the sequence of the modified matrix protein (M) is the amino acid sequence encoding the modified matrix protein (M) and has the following mutations as compared with SEQ ID NO:1: (i) mutation of glycine G to glutamic acid E at position 21, (ii) mutation of methionine M to alanine A at position 51, (iii) mutation of leucine L to phenylalanine F at position 111, and (iv) mutation of valine V to phenylalanine F at position 221; preferably, the sequence of the modified matrix protein (M) is a sequence as set forth in SEQ ID NO:3.

In one technical solution, the present disclosure relates to a recombinant oncolytic rhabdovirus, wherein the recombinant oncolytic rhabdovirus generates a modified matrix protein (M), wherein an amino acid sequence of the modified matrix protein (M) is the amino acid sequence as shown above; preferably, the recombinant oncolytic rhabdovirus is an attenuated oncolytic rhabdovirus.

In one technical solution, the present disclosure relates to a composition comprising an isolated recombinant oncolytic rhabdovirus, wherein the recombinant oncolytic rhabdovirus comprises a nucleic acid fragment, the nucleic acid fragment encodes a modified matrix protein (M), wherein an amino acid sequence of the modified matrix protein (M) is the amino acid sequence as shown above; preferably, the recombinant oncolytic rhabdovirus is an attenuated recombinant oncolytic rhabdovirus.

In another technical solution, the present disclosure relates to a composition further comprising a second oncolytic virus; preferably, the second oncolytic virus is one or more selected from the group consisting of a rhabdovirus, a vaccinia virus, a herpes virus, a measles virus, a Newcastle disease virus, an adenovirus, an alphavirus, a parvovirus, and an enterovirus strain; more preferably, the second oncolytic virus is an attenuated oncolytic virus; and most preferably, the second oncolytic virus is an attenuated rhabdovirus.

In another technical solution, the present disclosure relates to a composition further comprising a second antitumor preparation; preferably, the second antitumor preparation is an immunotherapeutic agent, a chemotherapeutic agent or a radiotherapeutic agent; more preferably, the second antitumor preparation is one or more selected from the group consisting of small molecules, macromolecules, cells, viral vectors, gene vectors, DNAs, RNAs, polypeptides and nanocomposites.

In one technical solution, the present disclosure relates to a vaccine, the vaccine comprises a therapeutically effective amount of one or more recombinant oncolytic rhabdoviruses, wherein said one or more recombinant oncolytic rhabdoviruses comprise the aforementioned modified matrix protein (M).

In another technical solution, the present disclosure relates to a vaccine which may further comprise the second oncolytic virus or the second antitumor preparation.

In one technical solution, the present disclosure relates to an isolated peptide encoded by an amino acid sequence, wherein the amino acid sequence comprises a sequence which is at least 80%, preferably at least 90%, more preferably at least 95% and most preferably at least 98% identical to an amino acid sequence of SEQ ID NO: 1, and the amino acid sequence has amino acid substitutions at position 21, position 51, position 111 and position 221 as compared with SEQ ID NO: 1.

In another technical solution, the amino acid sequence encoding the isolated peptide involved in the present disclosure has the following mutations: (i) mutation of glycine G to glutamic acid E at position 21, (ii) mutation of methionine M to alanine A at position 51, (iii) mutation of leucine L to phenylalanine F at position 111, and (iv) mutation of valine V to phenylalanine F at position 221; preferably, the amino acid sequence is a sequence as set forth in SEQ ID NO:3.

In one technical solution, the present disclosure relates to a nucleotide sequence for encoding the isolated peptide.

In one technical solution, the present disclosure relates to use of the composition comprising the isolated recombinant oncolytic rhabdovirus or the vaccine in preparation of a drug for killing abnormally proliferating cells, inducing and promoting antitumor immune response or eliminating immunosuppression in a microenvironment of a tumor tissue.

In another technical solution, in the above-mentioned use of the present disclosure, the abnormally proliferating cells are contained in the body of a patient.

In another technical solution, in the above-mentioned use of the present disclosure, the abnormally proliferating cells are selected from tumor cells or tumor tissue-related cells; preferably, the tumor cells are cancer cells; and more preferably, the cancer cells are metastatic cancer cells.

In one technical solution, the present disclosure relates to use of the composition comprising the isolated recombinant oncolytic rhabdovirus or the vaccine in preparation of a drug for treating a patient suffering from tumor.

In one technical solution, the present disclosure relates to a method for slowly and continuously killing abnormally proliferating cells, comprising a step of contacting the abnormally proliferating cells with the recombinant oncolytic rhabdovirus, the composition comprising the isolated recombinant oncolytic rhabdovirus or the vaccine.

In another technical solution, the present disclosure relates to a method for slowly and continuously killing abnormally proliferating cells, wherein the abnormally proliferating cells are contained in the body of a patient.

In another technical solution, the present disclosure relates to a method for slowly and continuously killing abnormally proliferating cells, wherein the abnormally proliferating cells are selected from tumor cells or tumor tissue-related cells; preferably, the tumor cells are cancer cells; and more preferably, the cancer cells are metastatic cancer cells.

In another technical solution, the present disclosure relates to a method for slowly and continuously killing abnormally proliferating cells, wherein the recombinant oncolytic rhabdovirus, the composition comprising the isolated recombinant oncolytic rhabdovirus, or the vaccine is administered to a patient.

In another technical solution, the present disclosure relates to a method for slowly and continuously killing abnormally proliferating cells, wherein the recombinant oncolytic rhabdovirus, the composition comprising the isolated recombinant oncolytic rhabdovirus, or the vaccine is administered via one or more administration modes selected from the group consisting of intraperitoneal administration, intravenous administration, intraarterial administration, intramuscular administration, intradermal administration, intratumoral administration, subcutaneous administration and intranasal administration; preferably, administration routes of the administration modes include one or more selected from the group consisting of endoscopy, celioscopy, intervention, minimal invasive surgery and traditional surgery.

In another technical solution, the present disclosure relates to a method for slowly and continuously killing abnormally proliferating cells, wherein the method further comprises a step of administering a second antitumor therapy.

In another technical solution, the present disclosure relates to a method for slowly and continuously killing abnormally proliferating cells, wherein the second antitumor therapy is administering a second oncolytic virus.

In another technical solution, the present disclosure relates to a method for slowly and continuously killing abnormally proliferating cells, wherein the second oncolytic virus is one or more selected from the group consisting of a rhabdovirus, a vaccinia virus, a herpes virus, a measles virus, a Newcastle disease virus, an adenovirus, an alphavirus, a parvovirus, and an enterovirus strain; more preferably, the second oncolytic virus is an attenuated oncolytic virus; and most preferably, the second oncolytic virus is an attenuated rhabdovirus.

In another technical solution, the present disclosure relates to a method for slowly and continuously killing abnormally proliferating cells, wherein the second antitumor therapy is one or more selected from the group consisting of chemotherapy, radiotherapy, immunotherapy and surgical therapy.

In one technical solution, the present disclosure relates to a method for inducing immune response in a subject, wherein the method comprises administering one or more selected from the group consisting of the recombinant oncolytic rhabdovirus, the composition comprising the isolated recombinant oncolytic rhabdovirus and the vaccine to a subject.

In one technical solution, the present disclosure relates to a method for inducing and promoting antitumor immune response or eliminating immunosuppression in a microenvironment of a tumor tissue, comprising a step of contacting a tumor or a tumor tissue with the recombinant oncolytic rhabdovirus, the composition comprising the isolated recombinant oncolytic rhabdovirus, or the vaccine.

Advantageous Effects of the Disclosure

By utilizing gene recombination technique, the present disclosure provides an attenuated strain of oncolytic rhabdovirus which is capable of effectively reducing the toxicity of the virus in normal somatic cells, while ensuring high selectivity for abnormally proliferating cells with respect to normal cells and infecting tumor cells to produce good oncolytic effect. Meanwhile, the aforementioned attenuated strain has the characteristics of exhibiting continuous replication and expression, having a high titer, stimulating an immune response in the local microenvironment of a tumor as well as maintaining high selectivity in the infection of tumor cells while exerting low toxicity to normal cells. In one technical solution, the attenuated strain of oncolytic rhabdovirus described in the present disclosure has the effect of inducing and promoting antitumor immune response and eliminating immunosuppression in the microenvironment of a tumor tissue, which has great significance in the clinical treatment of tumors.

BRIEF DESCRIPTION OF THE DRAWINGS

FIG. 1 shows the virus rescue of attenuated VSV oncolytic viruses with single-point or multipoint random mutations (RV-Mut).

DETAILED DESCRIPTION

Definitions

Figure 2:
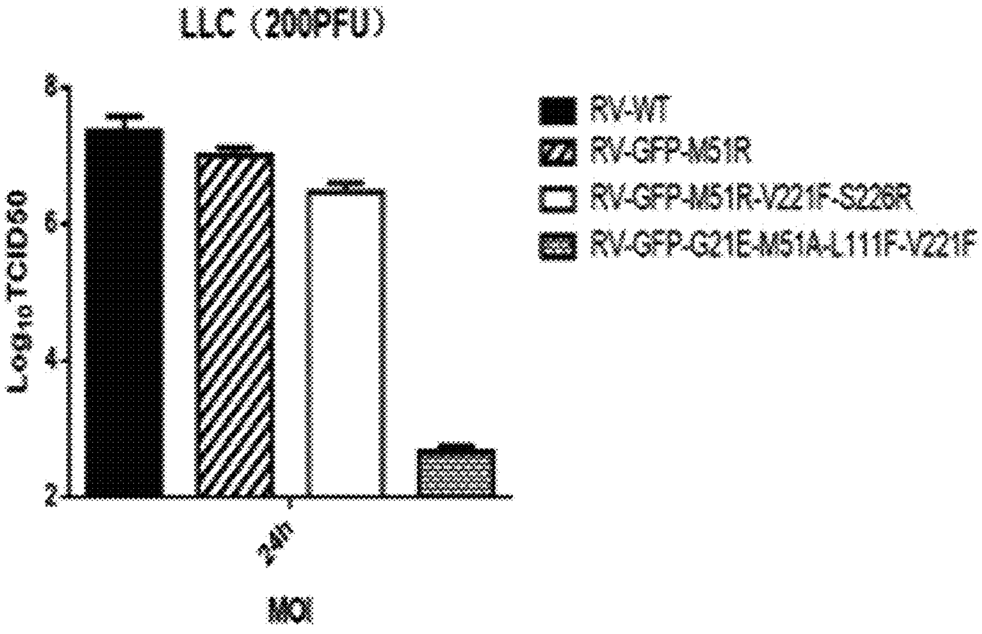
FIG. 2 shows the virus replication of different attenuated strains including RV-4Mut at different time points in LLC tumor cells.
Figure 2:
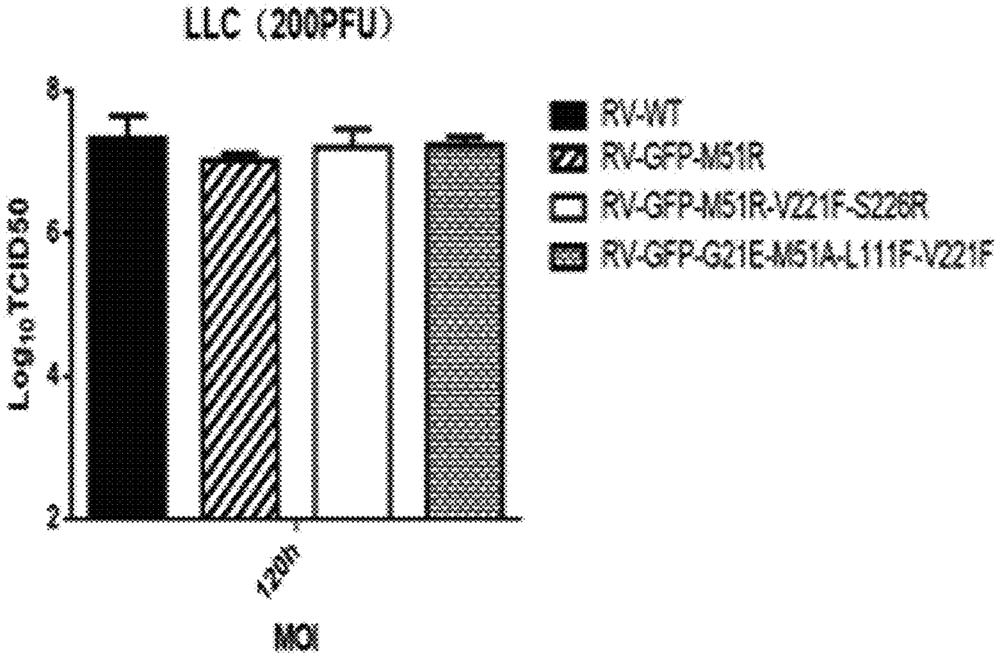

When used in combination with the term "comprise" in claims and/or specification, the wording "a" or "an" may refer to "one", but may also refer to "one or more", "at least one" and "one or more than one".

As used in claims and specification, the wording "comprise", "have", "include" or "contain" means inclusive or open-ended, and does not exclude additional and unreferenced elements, method or steps.

Throughout the application document, the term "about" means that a value includes the standard deviation of the error of the device or method used to determine the value.

Although the definition of the term "or" as being an alternative only and as "and/or" are both supported by the disclosed content, the term "or" in claims means "and/or" unless it is explicitly indicated that the term "or" only means an alternative or the alternatives are mutually exclusive.

When used in claims and/or specification, the term "inhibition", "reduction", "prevention" or any variation of these terms includes any measurable reduction or complete inhibition for the purpose of achieving the desired results (for example, treatment of tumor). Desired results include but are not limited to the relief, reduction, slowing or eradication of a cancer, a hyperproliferative condition or a symptom related to a cancer, as well as the improved quality or extension of life.

The vaccination method of the present disclosure may be used for treating tumors in a mammal. Alternatively, the vaccination method of the present disclosure may be used for treating cancers in a mammal. The term "cancer" used in the present disclosure includes any cancer, including but not limited to melanoma, sarcoma, lymphoma, cancer (for example, brain cancer, breast cancer, liver cancer, gastric cancer, lung cancer, and colon cancer) and leukemia.

The term "mammal" refers to human and non-human mammals.

The method of the present disclosure comprises administering to a mammal an oncolytic vector expressing a tumor antigen to which the mammal has pre-existing immunity. The term "pre-existing immunity" used in the present disclosure is intended to include the immunity induced by vaccination with an antigen and the immunity naturally existing in a mammal.

The term "RV virus" used in the present disclosure refers to an attenuated VSV oncolytic rhabdovirus. The term "RV-Mut" refers to an oncolytic rhabdovirus having mutation(s) compared to the wild-type VSV oncolytic rhabdovirus.

Technical Solutions

According to a research paper published by Claus O. Wilke, et al, when comparing MuddSummer strain (a subtype of Indiana strain of VSV) with the other two virus strains, it has been found that, when being passaged for 25 generations, MuddSummer strain has the least mutations with the sites of synonymous mutations mainly concentrated on two viral genes (M and G) and has the best stability. Therefore, the development of VSV-MuddSummer subtype strain into an oncolytic viral vector has inherent advantages.

In one embodiment of the present disclosure, in order to develop the pre-existing immunity, the method of the present disclosure comprises a step of vaccinating a mammal with a tumor antigen suitable for inducing immune response against target tumor cells. For example, the tumor antigen may be a tumor-associated antigen (TAA), such as a substance generated in tumor cells that trigger an immune response in a mammal. Examples of such antigens include oncofetal antigens (such as alpha-fetoprotein (AFP)) and carcinoembryonic antigen (CEA), surface glycoproteins (such as CA 125), oncogenes (such as Her2), melanoma-associated antigens (such as dopachrome tautomerase (DCT)), GP100 and MART1, cancer-testis antigens (such as MAGE protein and NY-ESO1), viral oncogenes (such as HPV E6 and E7), and proteins that are ectopically expressed in tumors and are usually limited to embryonic tissues or extra-embryonic tissues (such as PLAC1). As those skilled in the art should understand, antigen(s) may be selected according to the type of cancer to be treated by the method of the present disclosure since one or more antigens may be particularly suitable for treating certain cancers. For example, as for the treatment of melanoma, a melanoma-associated antigen such as DCT may be used.

An antigen itself may be administered, or preferably, an antigen may be administered via a vector such as an adenovirus (Ad) vector, a poxvirus vector or a retroviral vector, a plasmid, or an antigen-loaded antigen presenting cell such as a dendritic cell. The method of introducing an antigen into a vector is known to those skilled in the art. In general, the vector may be modified to express the antigen. In this regard, the widely accepted recombination technique is used to integrate the nucleic acid fragment encoding the selected antigen into the selected vector.

An antigen is administered to a mammal by any one of the several methods below, including but not limited to intravenous administration, intramuscular administration or intranasal administration. As those skilled in the art should understand, an antigen or a vector loaded with an antigen may be administered in a suitable vehicle (such as saline or other suitable buffer solutions). After vaccinated with the selected tumor antigen, the mammal produces an immune response within the interval of immune response, for example, the immune response may be produced within about 4 days and last for up to several months, several years or possibly the whole lifetime.

The immune response to the antigen is developed by adopting a widely accepted technology to carry out vaccination with the antigen. Therefore, the selected antigen or a vector expressing the antigen may be administered to a mammal in an amount sufficient to induce immune response. As those skilled in the art should understand, the amount required to induce immune response will vary with a variety of factors, including, for example, the selected antigen, the vector used for delivering the antigen, and the breed, age, body type and the like of the mammal to be treated. In this regard, for example, an intramuscular administration of an adenovirus vector to a mouse in a minimum amount of at least about $10^7$ PFU is sufficient to induce immune response. As for the administration to human, the corresponding amount should be sufficient to induce immune response.

In another embodiment, the immune response to an antigen may be naturally generated in a mammal without the need of the first vaccination step to induce immune response. The naturally occurring immune response to the antigen may be induced by any previous exposure to the antigen.

Once the immune response is generated in a mammal within an appropriate immune response interval, such as at least about 24 hours, preferably at least about 2 to 4 days or longer such as at least about 1 week, an oncolytic virus expressing the tumor antigen is administered to the mammal in an amount suitable for oncolytic virus therapy. As those skilled in the art should understand, said amount may vary with the selected oncolytic virus and the mammal to be treated. For example, an intravenous administration of an oncolytic VSV to a mouse in a minimum amount of $10^8$ PFU is sufficient for oncolytic therapy. The corresponding amount may be sufficient for human use.

The transgene encoding the antigen may be integrated into a virus by using standard recombination technique, so as to prepare an oncolytic virus expressing the selected tumor antigen. For example, the transgene is integrated into the genome of the virus, or a plasmid integrated with the transgene is used to integrate the transgene into the virus. The method of the present disclosure has no particular limitation on the available oncolytic viruses, and said available oncolytic viruses may include any oncolytic virus that is capable of destroying tumor while being suitable for administration to a mammal.

In one embodiment, the present disclosure describes an attenuated rhabdovirus produced by a reverse genetic operating system, which is a novel recombinant system developed for gene therapy of tumor. An attenuated quadruple mutant of rhabdovirus (RV-4Mut) has been produced, and has been demonstrated to be safe and effective in systemic delivery in a variety of tumor models (tumor models with immune function).

In one embodiment, the attenuated quadruple mutant of the rhabdovirus of the present disclosure (and/or other oncolytic agents) may be used continuously without causing strong immune response against the therapeutic virus in the host. Based on this, the host may be treated with the same viral system for multiple times within a certain period of time, thereby prolonging the treatment time, further reducing the occurrence of the body's resistance to single drug and thus improving the therapeutic effects of tumor. The embodiments of the present disclosure include compositions and methods related to rhabdoviruses and the use thereof in antitumor therapy. These rhabdoviruses have the characteristic of being capable of killing tumor cells both in vivo and in vitro. In the present disclosure, the rhabdovirus may be an attenuated rhabdovirus or a genetically engineered variant of an attenuated rhabdovirus. The virus described in this application may be used in combination with other rhabdoviruses.

In one embodiment of the present disclosure, an attenuated rhabdovirus and a composition comprising the attenuated rhabdovirus are included. The sequence of said attenuated rhabdovirus encodes a variant M protein that has at least or at most 20%, 30%, 40%, 50%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, 100% (including all ranges and percentages between these values) amino acid identity with the M protein of the attenuated rhabdovirus (that is, the amino acid sequence as set forth in SEQ ID NO:1). The above-mentioned M proteins of the attenuated rhabdovirus having a certain percentage of identity with each other means that the M protein of the attenuated rhabdovirus has conservative mutations capable of normally maintaining the function of the protein. A representative example of conservative mutations is conservative substitution. Conservative substitution refers to, for example, a mutation wherein substitution takes place mutually among Phe, Trp and Tyr in a case where the substitution site is an aromatic amino acid; a mutation wherein substitution takes place mutually among Leu, Ile and Val in a case where the substitution site is a hydrophobic amino acid; a mutation wherein substitution takes place mutually between Gln and Asn in a case where the substitution site is a polar amino acid; a mutation wherein substitution takes place mutually among Lys, Arg and His in a case where the substitution site is a basic amino acid; a mutation wherein substitution takes place mutually between Asp and Glu in a case where the substitution site is an acidic amino acid; and a mutation wherein substitution takes place mutually between Ser and Thr in a case where the substitution site is an amino acid having a hydroxyl group. As substitutions considered as conservative substitutions, there may be specifically exemplified substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Gly, Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val. Furthermore, the above-mentioned synonymous mutation of the M protein of the attenuated rhabdovirus also include naturally occurring mutations which are attributed to the gene-derived individual difference, difference in strains, difference in species and the like of the rhabdovirus.

In some cases, as for individual random mutations, although each single-mutant strain may reduce the toxic effect of the virus on normal healthy cells, it is highly likely that the virus may become more toxic than the wild-type virus in tumor cells once the above-mentioned multiple sets of individual random mutations are combined. Therefore, the therapeutic index of the recombinant oncolytic rhabdovirus of the present disclosure is unexpectedly increased, which is an unexpected finding achieved based on the large-scale screening process of the attenuated strains in vitro. When multiple single-mutant attenuated strains undergo simultaneous mutations of multiple genes, most viruses lose infectivity in both tumor cells and normal cells, and a few of the viruses show virulence enhancement with enhanced cytotoxicity. It has been unexpectedly found in the present disclosure that the four amino acid mutations of RV-4Mut do not cause the virulence enhancement of the virus itself, while continuously retaining the tumor-killing property. Although it has been found at cell level in vitro that the time point of the lysis of tumor cells is delayed, the specific tumor-killing property is completely retained, and the most rare and commendable advantage is that RV-4Mut does not have any toxicity to normal cells and fully meets the requirements for biosafety.

The methods and the compositions of the present disclosure may comprise a second therapeutic virus, such as an oncolytic virus or a replication-defective virus. Oncolysis generally refers to the ability to kill tumor cells, lyse tumor cells or prevent the growth of tumor cells. An oncolytic virus refers to a virus that is able to replicate in tumor cells to a certain degree, cause the death, lysis (oncolysis) or growth arrest of tumor cells, and usually has tiny toxic effect on non-tumor cells. The second virus includes but is not limited to a rhabdovirus, a vaccinia virus, a herpes virus, a measles virus, a Newcastle disease virus, an adenovirus, an alphavirus, a parvovirus, an enterovirus strain, and the like.

The embodiments of the present disclosure comprise compositions and methods related to rhabdoviruses comprising heterologous N protein, P protein, M protein, G protein and/or L protein as well as the use thereof in antitumor therapy. Such rhabdovirus has tumor cell-killing property both in vivo and in vitro. Therefore, the VSV virus as described in the present disclosure may be further modified by integrating heterologous N protein, P protein, M protein, G protein and/or L protein. As used in the present disclosure, the heterologous N protein, P protein, M protein, G protein and/or L protein include the N protein, P protein, M protein, G protein and/or L protein of rhabdovirus.

The method of the present disclosure may further comprise administering a second antitumor therapy, such as administering a second therapeutic virus. In certain aspects, the therapeutic virus may be an oncolytic virus, more particularly a VSV virus. In other aspects, the second antitumor therapy is administering a chemotherapeutic agent, a radiotherapeutic agent, an immunotherapeutic agent, surgery, or the like.

In another aspect, said composition is a pharmaceutically acceptable composition. Said composition may further comprise a second antitumor preparation, such as a chemotherapeutic agent, a radiotherapeutic agent or an immunotherapeutic agent.

Another embodiment of the present disclosure relates to a method for killing proliferative cells, and said method comprises contacting such cells with the composition comprising the isolated oncolytic rhabdovirus of the present disclosure.

Another embodiment of the present disclosure relates to the treatment of cancer patients, including administering an effective amount of the composition comprising oncolytic rhabdovirus of the present disclosure.

In certain aspects of the present disclosure, cells may be contained in the body of a patient, and said cells may be proliferative, neoplastic, precancerous or metastatic cells. Rhabdoviruses may be administered to a patient having cells that are susceptible to being killed by at least one of the rhabdoviruses, a treatment regimen comprising the rhabdovirus(es) or a composition comprising the rhabdovirus(es). The administration of the therapeutic composition may be carried out 1, 2, 3, 4, 5, 6, 7, 8, 9, 10 times or more times using 1, 2, 3, 4, 5, 6, 7, 8, 9, 10 kinds or more kinds of rhabdoviruses or recombinant rhabdoviruses (alone or combined in various manners). The administration may be intraperitoneal administration, intravenous administration, intraarterial administration, intramuscular administration, intradermal administration, subcutaneous administration or nasal administration. In certain aspects, the composition is administered systemically, especially via intravascular administration, including injection, perfusion, and the like.

EXAMPLES

Other objects, features and advantages of the present disclosure will become apparent from the following detailed description. However, it should be understood that the detailed description and specific Examples (although representing the specific embodiments of the present disclosure) are given for explanatory purposes only, since various changes and modifications made within the spirit and scope of the present disclosure will become apparent to those skilled in the art after reading this detailed description.

The reagents and consumables used in the present disclosure were as follows: PBS (Hyclone SH30256.01), DMEM high glucose medium (Gibco C11995500), RPMI1640 (Gibco C22400500CP), double antibody (Gibco 15140-122), fetal bovine serum (Gibco 10099141), Opti-MEM® I Reduced Serum Medium (Gibco 31985-070), Lipofectamine LTX (Invitrogen 15338100), 96-well cell culture plate (Corning 3599), 6-well cell culture plate (Corning 3516), 0.22 μm filter (Millipore SLGP033rb), DMSO (Macklin D806645), and thiazolyl blue (Sigma M2128).

Example 1: Virus Rescue of the Attenuated Mutant Strain (RV-Mut) Constructed Based on VSV Oncolytic Rhabdovirus Different attenuated strain systems were constructed based on the efficient rescue system of VSV virus and the virus rescue of viruses with single-point or multipoint random mutation(s) was observed, so as to confirm whether the virus particles could be obtained or not if the M protein of VSV virus is arbitrarily mutated (that is, whether or not the virus particles could be rescued in case of arbitrary mutation).

The specific steps of the construction of the above-mentioned virus rescue system were as follows.

1. BSR-T7 cells were seeded in a 6-well plate so as to enable the cell density to reach $4\times10^5$ cells/well. vT7 was added 14 h to 16 h after the seeding, and transfection was carried out after the cells were infected with the virus for 4 h.

2. The plasmid was diluted with opti-MEM culture medium, in which the total amount of the plasmid was 5 μg. 7.5 μl of PLUS Reagent was further added. 10 μl of Lipofectamine LTX was diluted with the culture medium.

3. The LTX mixed liquid and the DNA mixed liquid were mixed in equal volume and the mixture was incubated at room temperature.

4. The culture medium in the 6-well plate was replaced with Opti-MEM culture medium. The resulting mixed liquid in step 3 was added dropwise into the 6-well plate in which cells were cultured, and the 6-well plate was shaken gently so as to allow the mixed liquid to be evenly distributed in the 6-well plate.

5. After 6 h to 8 h of transfection, the transfection reagent was aspirated and removed, and the fresh complete culture medium was added.

6. After 72 h of cultivation, the cell supernatant was harvested and filtrated with a 0.22-μm filter.

A conventional method in the art was utilized to test whether the virus particles were successfully rescued. The test results of the success rates of virus packaging were as shown in FIG. 1.

The results in FIG. 1 demonstrated that, the amino acid at position 111 of the M protein of RV virus could only be mutated from leucine to phenylalanine while being mutated to other amino acids seriously affected the rescue of virus particles, the amino acid at position 221 of the M protein of the virus could only be replaced with phenylalanine and the recombinant virus could not be produced if the amino acid at this position was replaced with alanine.

The statistical list of the success rates of virus packaging as shown in FIG. 1 reflected that, an attenuated strain could be obtained by mutating the pathogenic gene M at specific sites, and the selection of amino acid mutation was not arbitrary and needed to follow specific principles instead, thus being able to produce specific virus particles.

Example 2: Determination of the Virus Titers of Different RV-Mut Virus Strains

In MEF/LLC cell culture fluid, 200 PFU of the following viruses were respectively added: VSV-GFP-WT, RV-GFP-M51R, RV-GFP-M51R-V221F-S226R (RV-3Mut), and RV-GFP-G21E-M51A-L111F-V221F (RV-4Mut). The virus titers ($TCID_{50}$) of these virus strains were determined.

The specific steps for determining the titers of the above-mentioned viruses were as follows.

1. 3 mL of Vero (LLC/Hela) cell suspension was added to each well of the 6-well culture plate, so as to enable the cell density to reach $4\times10^5$ cells/well (6 wells in total). The cells were incubated at 37° C. in 5% $CO_2$ atmosphere for 16 h.

2. 200 PFU of the viruses (VSV-GFP-WT, RV-GFP-M51R, RV-GFP-M51R-V221F-S226R, and RV-GFP-G21E-M51A-L111F-V221F) were respectively added to each well, and two wells containing normal cells were set as control groups. 100 μl of the cell supernatant was harvested at each of the following time points: 12 h, 24 h, 48 h, 72 h, 80 h, and 96 h.

3. 100 μl of Vero cell suspension was added to each well of a 96-well culture plate, so as to enable the cell density to reach $1\times10^4$ cells/well. The cells were incubated at 37° C. in 5% $CO_2$ atmosphere for 16 h.

4. The supernatant harvested in step 2 was serially diluted by 10 times in 1.5-ml EP tubes, so as to achieve 11 concentrations in total (ranging from $10^{-1}$ to $10^{-11}$ of the original concentration).

5. The diluted supernatants were inoculated into the 96-well culture plate, each column (8 wells in total) was inoculated with the diluted supernatant of each concentration, and each well was inoculated with 100 μl of the diluted supernatant. One column containing normal cells was set as the control group.

6. After 48 h, the fluorescence of cells in each well was observed, and a well was recorded as infected if fluorescence was observed.

7. $TCID_{50}$ was calculated by Karber's method.

Figure 3:
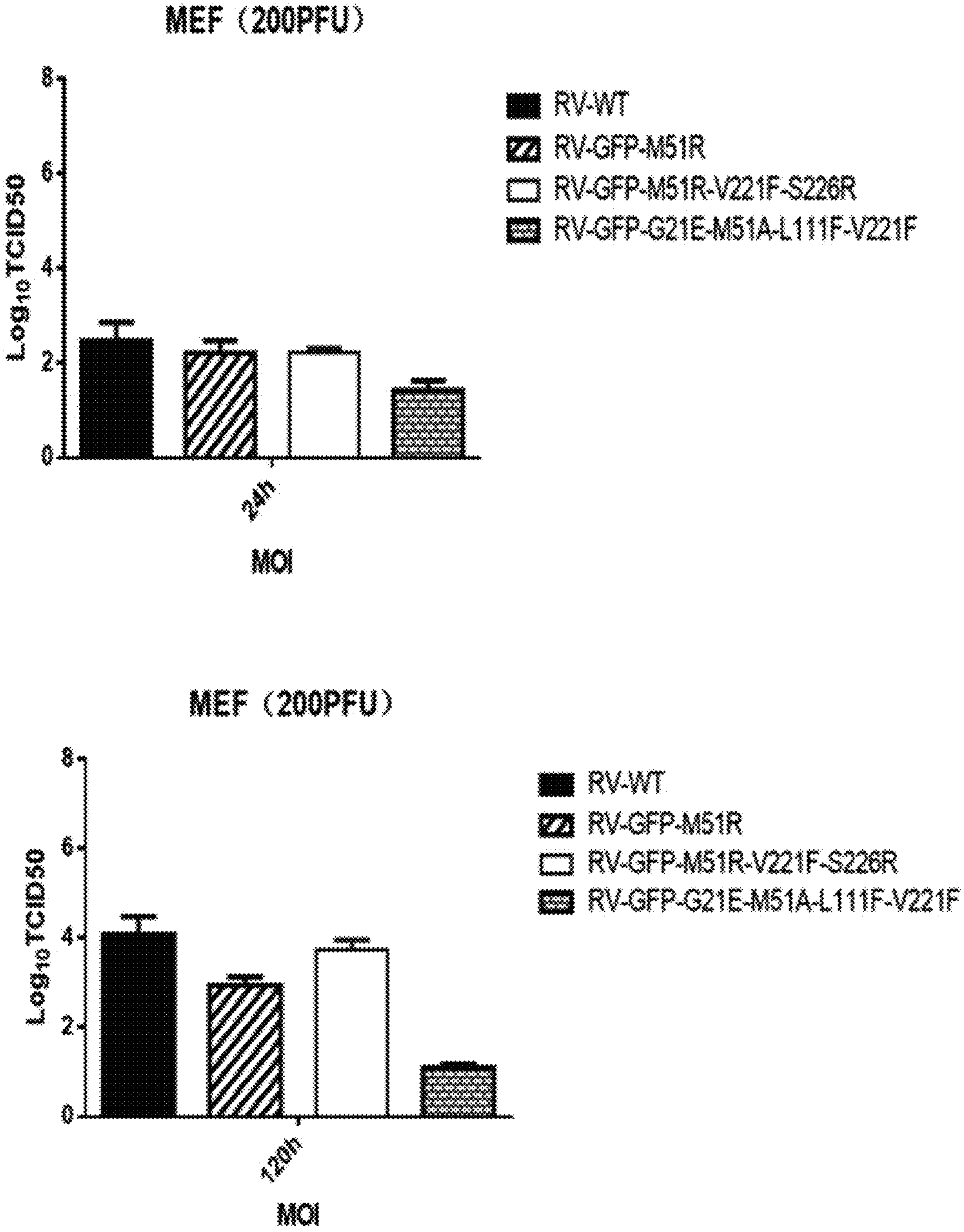
FIG. 3 shows the virus replication of different attenuated strains including RV-4Mut at different time points in normal cells.

The determination results of the titers of the above-mentioned viruses were as shown in FIG. 2 and FIG. 3.

As could be seen from FIG. 2, in in-vitro tumor cells, as for RV-4Mut, the number of the virus particles replicated and released into the supernatant during early infection was significantly reduced when compared with the viruses as control. However, when the infection period lasted for 5 days, the viral load of the tumor cells infected with RV-4Mut tended to be consistent with that of the wild-type virus, thereby proving that RV-4Mut had the characteristic of slowly infecting tumor cells.

As could be seen from FIG. 3, when the RV-4Mut attenuated strain infected normal fibroblasts, the viral load in the original supernatant was 200 PFU, the virus titers of different attenuated strains in the supernatants were determined at two time points (24 h and 120 h). It was found that, as for RV-4Mut attenuated strain group, the number of virus particles was reduced as compared with that in the original supernatant (the number of virus particles was significantly reduced in the supernatant after 120 h of infection), while there were different degrees of increase in the number of virus particles in each control group. This indicated that RV-4Mut strain did not have the ability to replicate in normal fibroblasts while the wild-type virus strain and the virus strains as control (RV-M51R and RV-3Mut) still had relatively strong infection and replication ability (as could be seen from FIG. 3, there were up to three orders of magnitude difference between the infection and replication ability of RV-4Mut attenuated strain and those of the wild-type virus strain and the virus strains as control (RV-M51R and RV-3Mut)).

Example 3: Comparison and Determination of the In-Vitro Killing Effects of RV-4Mut with Different Viral Titers on Different Tumor Cells The in-vitro killing effects of RV-4Mut attenuated strain with different viral titers on different tumor cells were determined by MTT detection method.

The specific steps of the above detection method were as follows.

1. 100 μl of Vero (LLC/Hela/MEF/MC38) cell suspension was added to each well of a 96-well culture plate, so as to enable the cell density to reach $1\times10^4$ cells/well. The cells were incubated at 37° C. in 5% $CO_2$ atmosphere for 16 h.

2. The viruses VSV-GFP-WT, RV-GFP-M51R, RV-GFP-M51R-V221F-S226R (RV-3Mut) and RV-GFP-G21E-M51A-L111F-V221F (RV-4Mut) were respectively diluted to have an MOI (multiplicity of infection) of 0.001, 0.01, 0.1 and 1.0, the diluted resultant of each gradient was inoculated into 4 wells (100 μl per well). The cells were incubated at 37° C. in 5% $CO_2$ atmosphere for 40 h.

3. The supernatant in the 96-well culture plate was discarded, fresh culture medium was added, and MTT solution was added (20 μL/well). The cells were incubated at 37° C. in 5% $CO_2$ atmosphere for 4 h.

4. The 96-well plate was centrifuged at room temperature for 5 minutes and the rotation speed was set to 2500 rpm/minute.

5. A 1-mL disposable sterile syringe was used to gently aspirate the supernatant.

6. DMSO was added to each well (100 μl/well), and the 96-well plate was left to stand at 37° C. for 10 minutes.

7. A multifunctional microplate reader was used to determine the OD value of each well at a wavelength of 570 nm or 490 nm after the 96-well plate was shaken for 2 minutes.

The determination results of the in-vitro killing effects of different virus strains mentioned above were as shown in FIG. 4 and FIG. 5.

Figure 4:
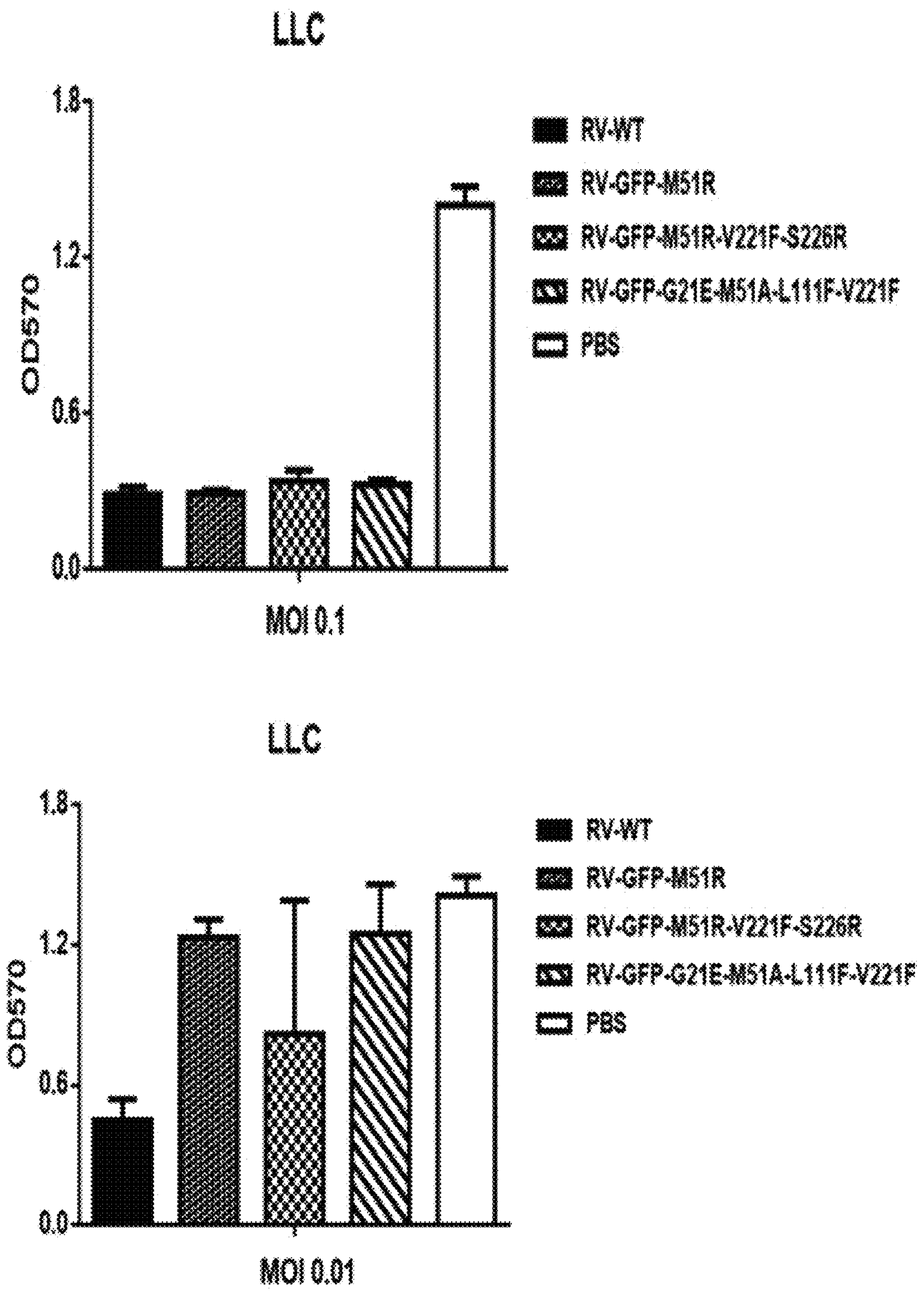
FIG. 4 shows the comparison of the in-vitro killing effects of different attenuated strains (including RV-4Mut) with different viral titers on different tumor cells.
Figure 4:
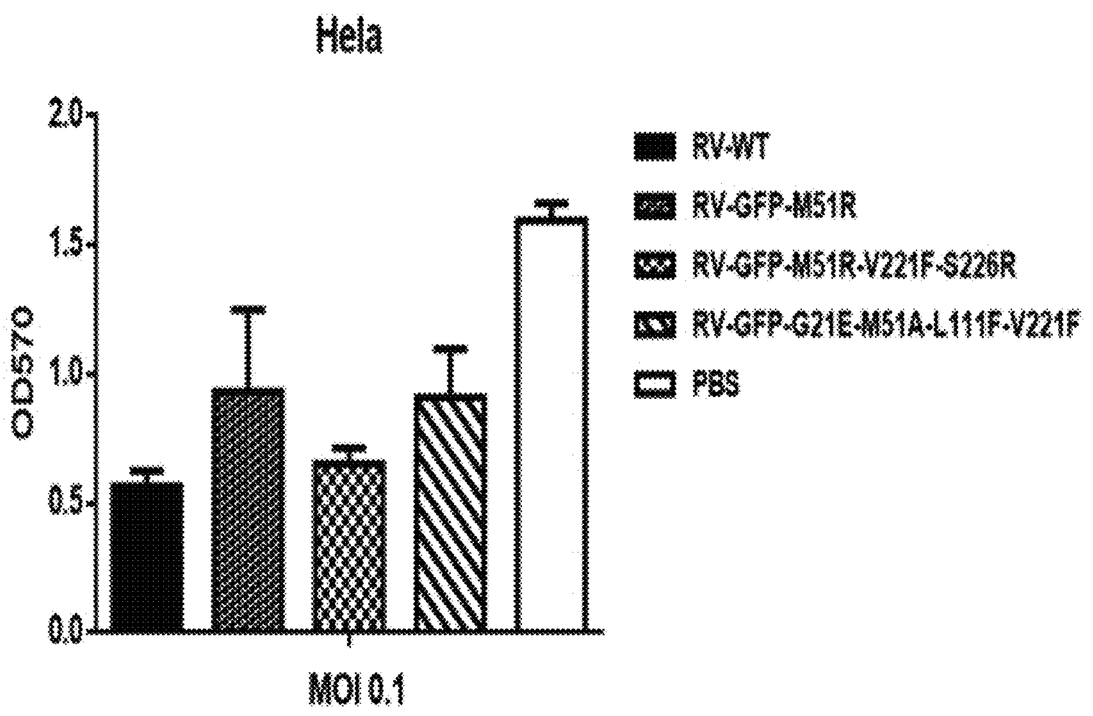
Figure 4:
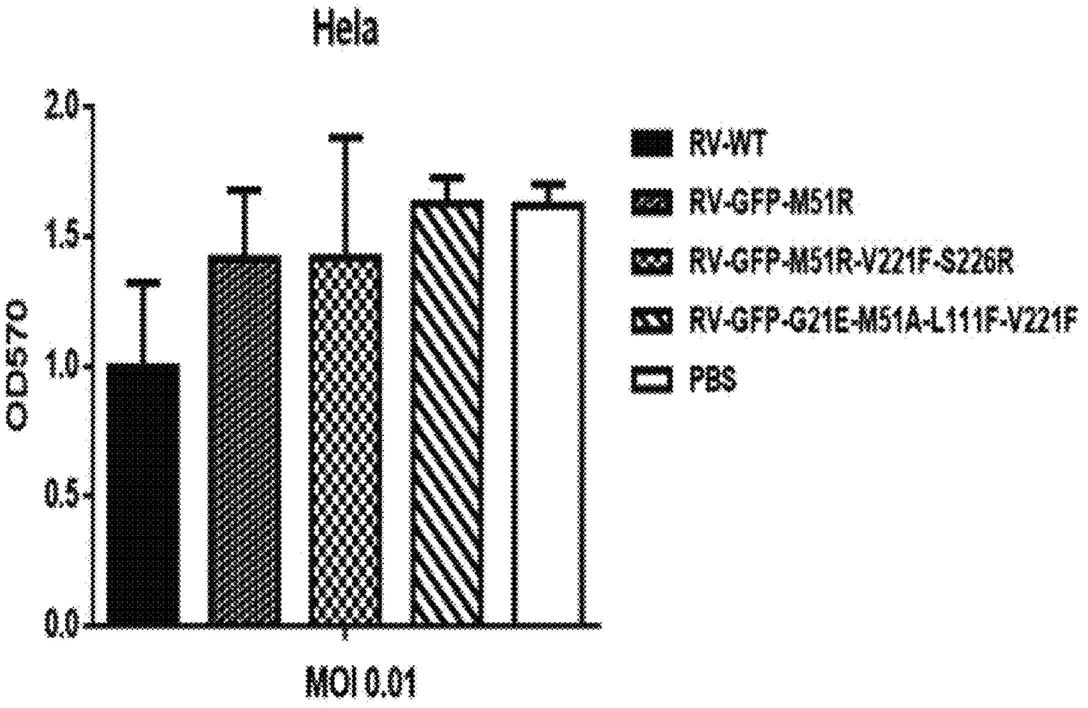

As shown in FIG. 4, when the multiplicity of infection of the virus was 0.01, RV-4Mut had slightly reduced ability to lyse LLC and Hela tumor cells as compared with the viruses in control groups, however, when the multiplicity of infection of RV-4Mut strain was increased to 0.1, the direct killing effect of RV-4Mut on tumor cells (LLC, Hela, or the like) was significantly improved and showed no significant difference when compared with the wild-type strain. This indicated that although RV-4Mut had mutations at four sites, it retained the tropism for tumor cells which was specific for the wild-type virus and had relatively strong ability to kill tumor cells continuously.

Figure 5:
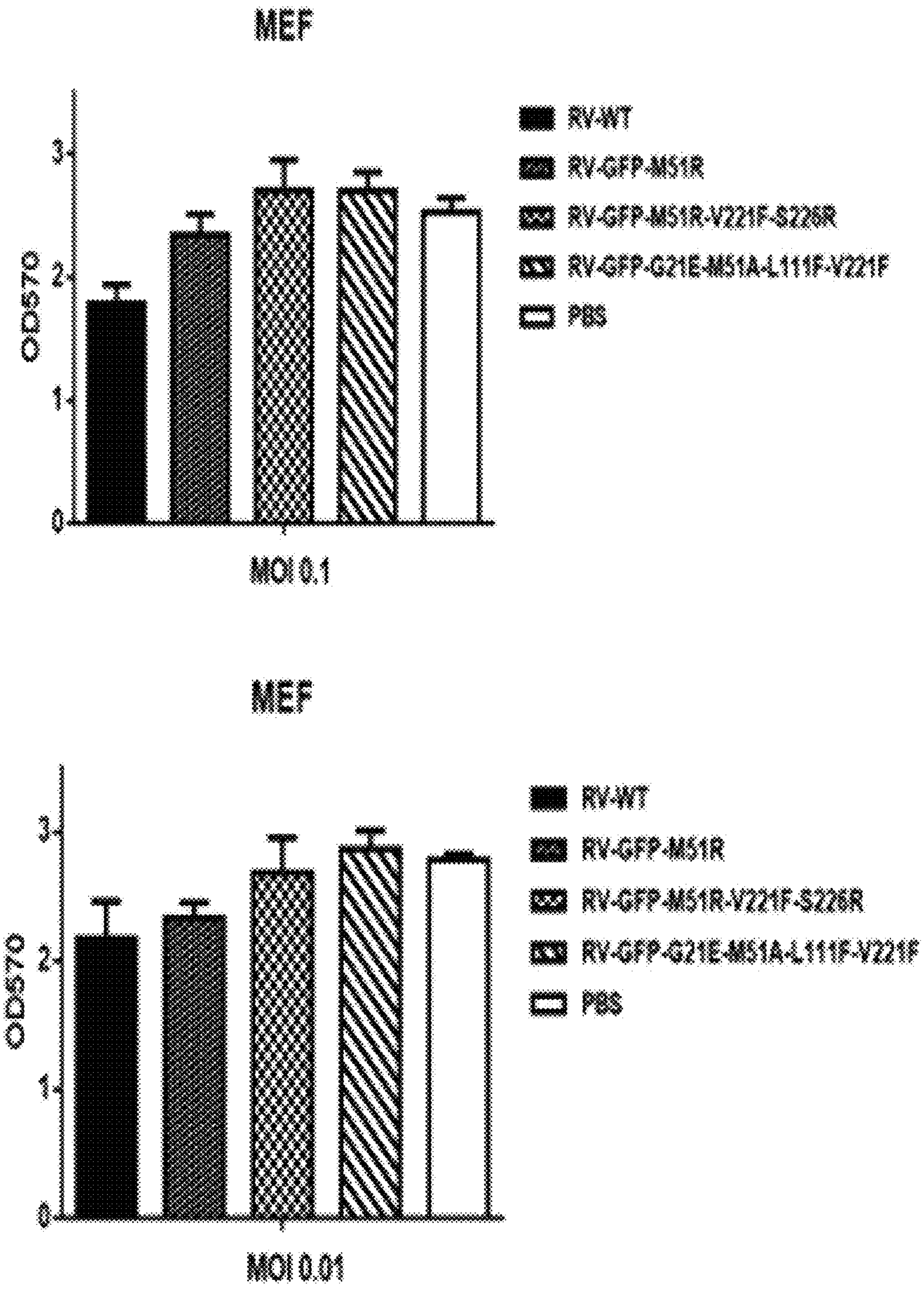
FIG. 5 shows the comparison of the toxic and side effects of different attenuated strains including RV-4Mut on MEF cells.

Meanwhile, the same experiment was repeated in MEF cells. As shown in FIG. 5, the experimental results showed that there was no significant difference between the toxic and side effects of RV-4Mut strain (having an MOI of 0.1 or 0.01) on normal cells and those observed in PBS group.

The results of the MTT experiment indicated that the quadruple mutant RV-4Mut had no significant toxic and side effects on normal cells in vitro and would not result in the apoptosis and necrosis of normal cells. However, both the wild-type strain and the RV-M51R virus in the control group had certain toxic and side effects on normal cells, and the wild-type strain had the strongest toxic and side effects. RV-4Mut virus strain had the lowest toxic and side effects and the best safety among the three attenuated strains.

Example 4: Expression of the Exogenous Gene GFP Chimerized in Different Attenuated Strains in Different Cells The expression of the exogenous gene GFP chimerized in different attenuated strains in different cells was determined by FACS flow cytometry.

The specific steps of the above-mentioned determination were as follows.

1. 100 μl of Vero (LLC/Hela/MEF) cell suspension was added to each well of 48-well culture plates, so as to enable the cell density to reach $2\times10^4$ cells/well. The cells were incubated at 37° C. in 5% $CO_2$ atmosphere for 16 h.

2. 100 PFU of the viruses (VSV-GFP-WT, RV-GFP-M51R, RV-GFP-M51R-V221F-S226R (RV-3Mut), and RV-GFP-G21E-M51A-L111F-V221F (RV-4Mut)) were respectively added to each well, each kind of virus was added to 21 wells, and 12 wells were set as the blank control group.

3. Cells were harvested at each time point (24 h, 36 h, 48 h, 60 h, 72 h, 84 h, and 96 h), the cells in three wells were harvested for each kind of virus and the cells in one well were harvested for the blank control group. The obtained cells were all re-suspended with 400 μl of PBS, 100 μL of the cell suspension was taken and analyzed by using Life Launch Attune N×T-Next flow cytometer, and the total number of GFP-positive cells was counted.

Figure 6:
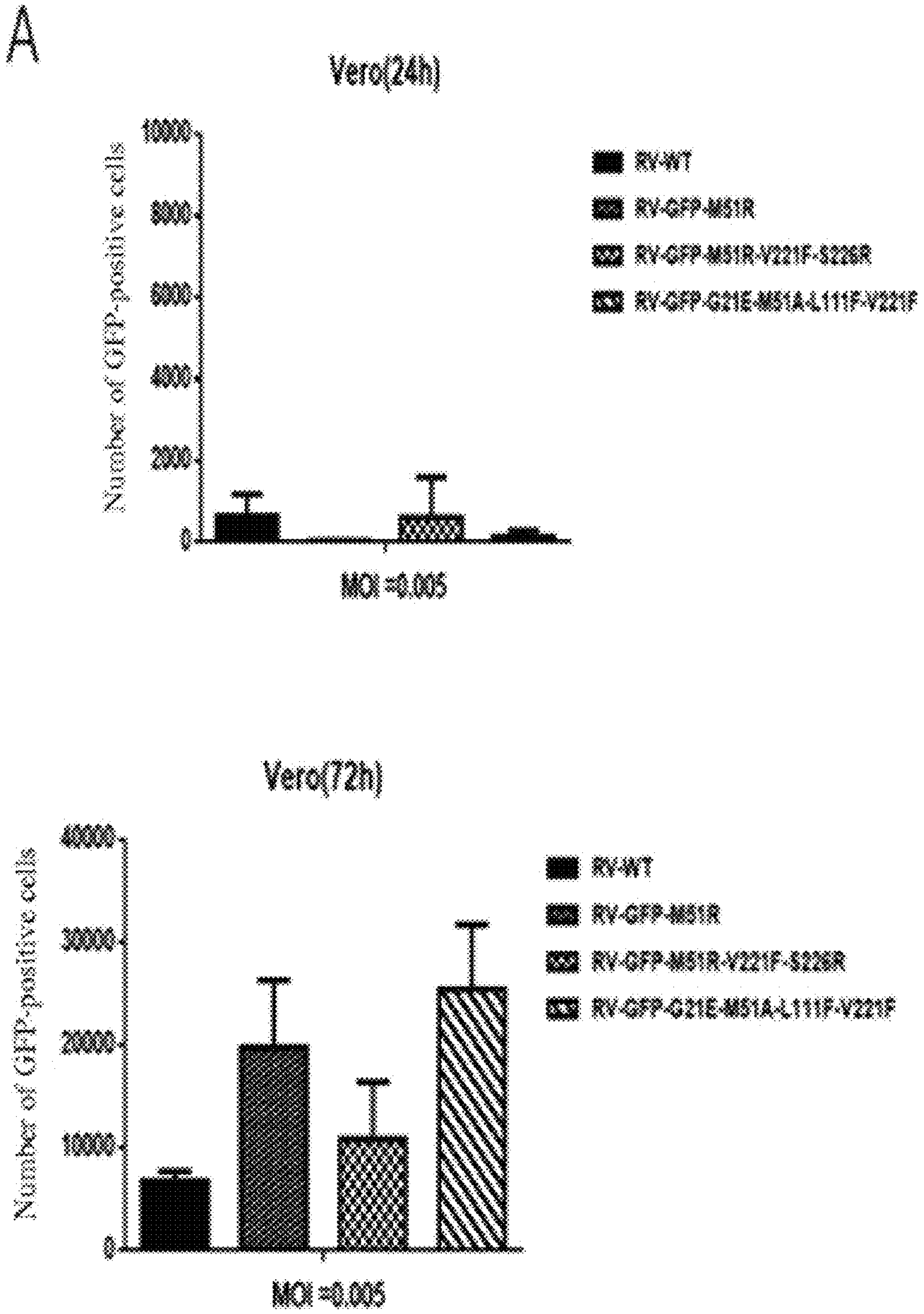
FIG. 6 shows the ability of different attenuated strains including RV-4Mut to continuously express the exogenous protein in different cells.
Figure 6:
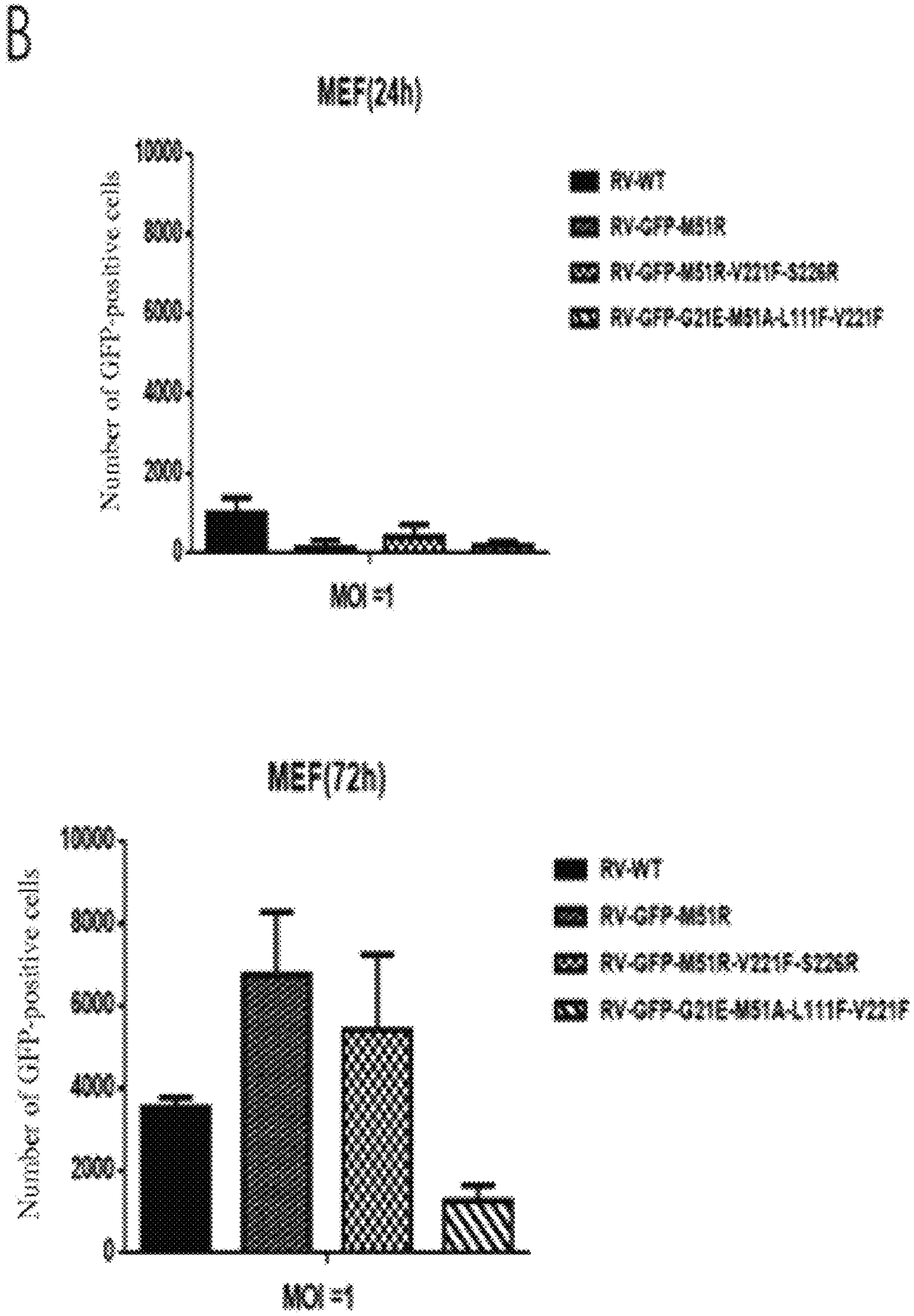

The determination results of the above-mentioned flow cytometry were as shown in FIG. 6.

As shown in FIG. 6A, in RV-4Mut virus strain group, the proportion of GFP-positive cells kept increasing among Vero cells (interferon-deficient cells) over time, and the proportion of GFP-positive cells infected with RV-4Mut virus strain exceeded the corresponding proportion of the wild-type virus 72 h after infection, indicating that compared with other candidate virus strains, RV-4Mut virus strain had stronger ability to continuously replicate and proliferate in cells defective in the expression ability of interferon, had prolonged replication time in Vero engineered cell line as compared with other control virus strains, and was more in line with the requirements of industrial-scale production.

However, in MEF cells, as shown in FIG. 6B, after the initial viral loads of the four viruses were increased by 200 fold, among all the viruses, RV-4Mut was the one that did not cause significantly increase of GFP-positive cells over time, while the interferon pathway in MEF cells was normal and MEF cells would respond rapidly when there was an infection caused by an external pathogen. The results shown in FIG. 6B (the infection and replication of viruses in MEF cells) proved that RV-4Mut had higher safety than the attenuated strains as control, and the underlying reason was that RV-4Mut was more sensitive to interferon.

Therefore, when the virus was subjected to GMP industrial production and the virus proliferated in Vero engineered cells (interferon-deficient cells), RV-4Mut virus strain had the ability to efficiently and continuously express the exogenous gene(s) and had an inherent advantage compared with the attenuated strains as control. Therefore, in reaction systems (reaction tanks) with the same volume, virus products with higher titer could be produced and prepared.

Example 5: Expression of the Same Exogenous Gene GFP Chimerized in Different Attenuated Strains in Different Tumor Cells (Hela and A549)

The expression of the same exogenous gene (GFP) chimerized in different attenuated strains in different tumor cells (Hela and A549) was determined by flow cytometry.

The specific steps of the above-mentioned determination were the same as those in Example 4.

Figure 7:
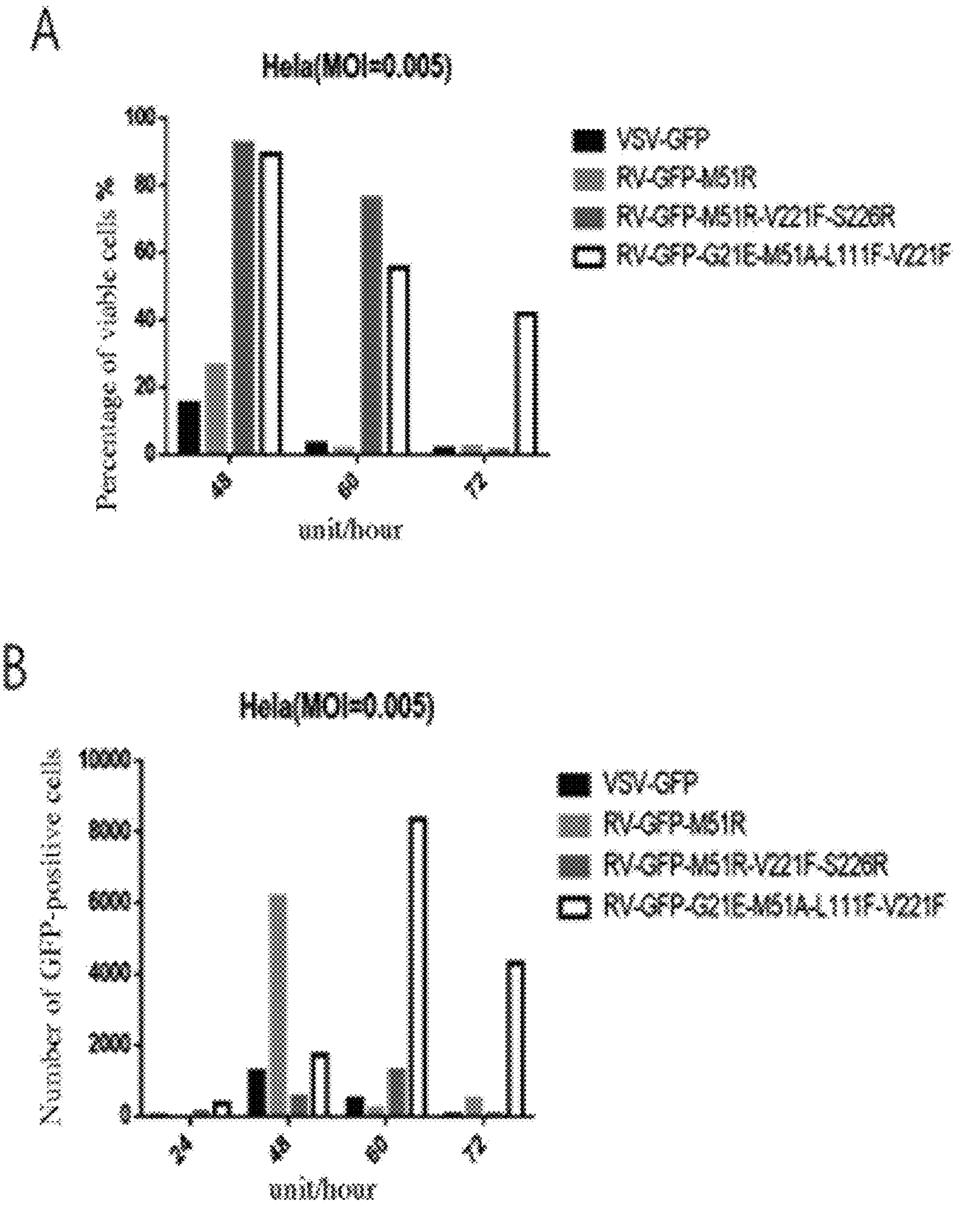
FIG. 7 shows the comparison of the ability of different attenuated strains including RV-4Mut to continuously replicate and express in human-derived tumor cells.
Figure 7:
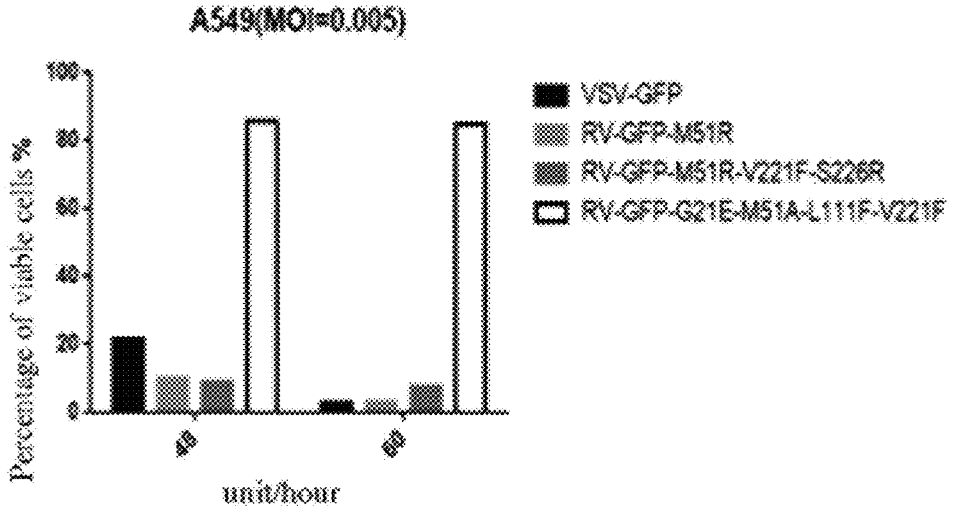
Figure 7:
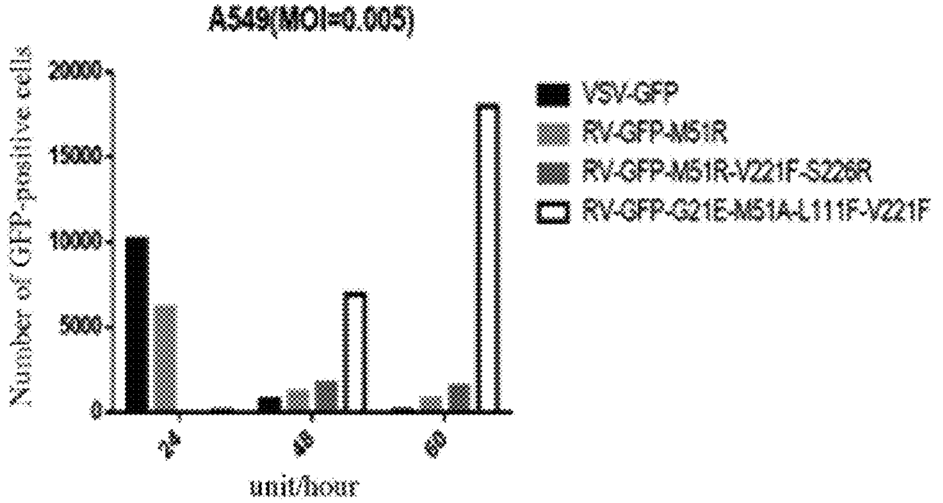

The determination results of the above-mentioned flow cytometry were as shown in FIG. 7.

From FIGS. 7A to 7D, according to the proportions of viable cells stained in the flow cytometry (FIGS. 7A to 7C), the proportion of viable cells in RV-4Mut group was relatively high in either Hela cells or A549 cells, which was beneficial for the replication of the virus in cells and finally enabled the expansion of the range of infected tumor cells by producing more virus particles.

As shown in FIGS. 7B to 7D, when Hela cells were infected with the quadruple mutant RV-4Mut in vitro, the proportion of GFP-positive cells kept increasing over time, the highest proportion was reached after 60 h, and then said proportion showed a tendency of decline. In A549 cells (FIG. 7D), at two time points (48 h and 60 h), the proportion of GFP-positive cells in RV-4Mut group was the highest as compared with those in the control groups, while said proportion was increased with the extension of the infection time and maintained a tendency consistent to that in Hela cells.

The above results indicated that, RV-4Mut had the ability to continuously replicate in tumor cells, and had better sustainability in the expression of the exogenous gene and showed significant advantages as compared with the control groups.

Example 6: Expression Levels of Antiviral Interferon in Different Cell Lines in Respond to Different Attenuated Virus Strains MEF cells or LLC tumor cells were infected with different attenuated strains in vitro, and the expression levels of antiviral interferon in different cell lines in respond to different attenuated virus strains were respectively determined by RT-PCR experimental technology.

The specific steps of the above-mentioned determination were as follows. TRIzol (Invitrogen) was used to extract total RNA from LLC cells and MEF cells, the total RNA was reversely transcripted into cDNA by using a reverse transcription kit (PrimeScript RT Reagent Kit with gDNA Eraser (Takara)), staining was carried out with LightCycler® 480 SYBR Green I Master (Roche) dye, and the Ct value of each gene was determined in LightCycler® 480 quantitative PCR system. ΔΔCt method was used to calculate the expression level of target genes IFN-β and VSV-G relative to that of the housekeeping gene GAPDH.

Figure 8:
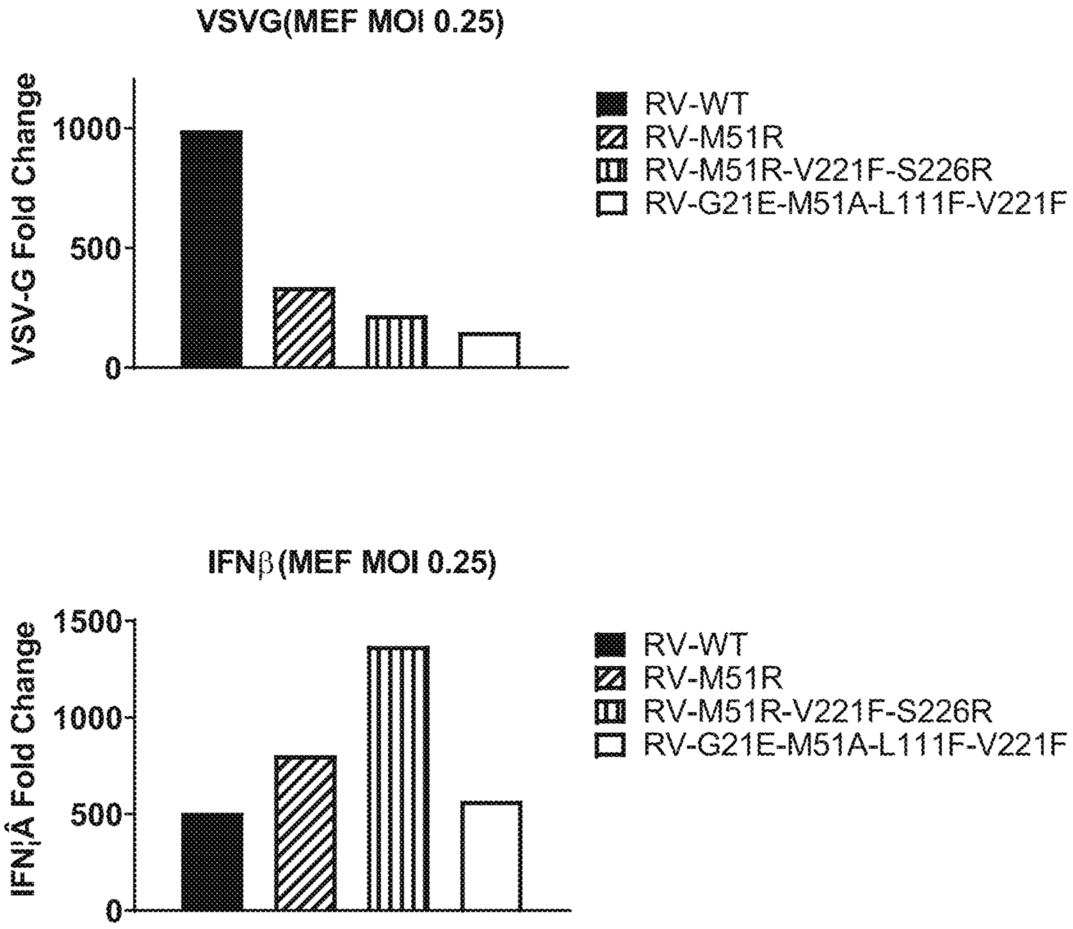
FIG. 8 shows the comparison of the ability of different attenuated strains including RV-4Mut to stimulate and thus induce the immune response to produce interferon in different cells.
Figure 8:
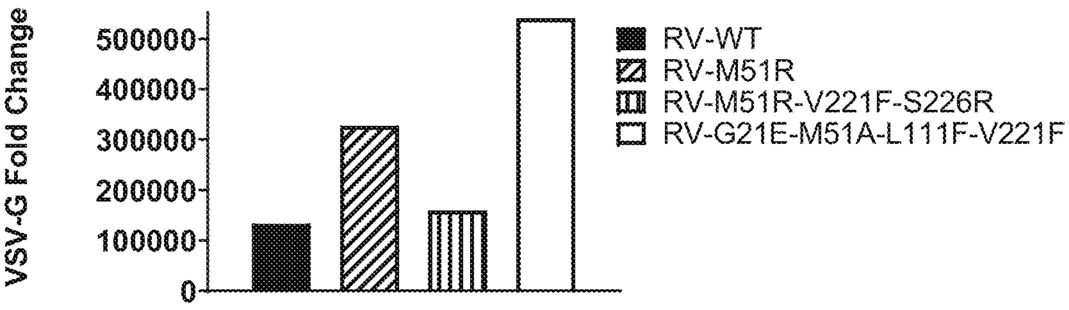
Figure 8:
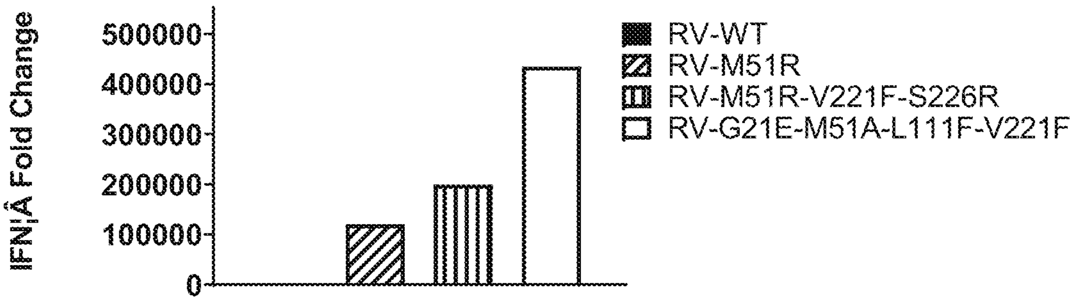

The determination results of the above determination were as shown in FIG. 8.

As shown in FIG. 8B and FIG. 8D, MEF cells and LLC tumor cells were respectively infected with four viruses. After MEF cells were infected with the above four viruses, the changes of the mRNA levels of IFN were as shown in FIG. 8B, and RV-4Mut had the lowest ability to induce interferon when compared with the other two attenuated strains. Also, the mRNA levels of VSV-G viruses that characterized the replication abilities were compared with those in control groups (FIG. 8A). The RNA level of RV-4Mut in MEF cells was very low, which further proved the high safety of RV-4Mut virus. Meanwhile, it was found by conducting the same experiment in LLC tumor cells that the observed phenomena were completely contrary to those observed in MEF cells, RV-4Mut attenuated strain stimulated LLC cells to express the highest level of interferon, and RV-4Mut also had the strongest ability to replicate in tumor cells as compared with the control groups (FIG. 8C).

The above experimental results proved that RV-4Mut infected tumor cells with high selectivity and also induced the enhancement of the ability of tumor cells to express interferon (the increasing level of interferon in tumor would significantly enhance the killing effects of local immune cells on tumor cells) at the same time, while the replication ability of the virus was not influenced. However, the interferon-expressing ability in normal cells was not significantly induced and enhanced by this RV-4Mut. The above findings further proved that RV-4Mut was capable of continuously stimulating the local immune cells around the tumor and generating sustained antitumor immune response.

Example 7: Verification of the Difference Between RV-4Mut and Other Virus Strains in Neurotoxicity In order to verify the difference between RV-4Mut and other virus strains in neurotoxicity, 6-week-old Balb/c mice were selected as experimental objects (10 mice in each group), and the mice in each group were respectively administered with 50 μl of the diluent of the virus ($10^8$ PFU/mL) (the aforementioned viruses were VSV-GFP-WT (i.e., RV-GFP), RV-GFP-M51R, RV-GFP-M51R-V221F-S226R (RV-3Mut) and RV-GFP-G21E-M51A-L111F-V221F (RV-4Mut), respectively) by nasal dripping every other day (twice in total). It had been known that the infection of the wild-type rhabdovirus via the nasal cavity would cause neural paralysis of the hind limbs in some experimental mice and would cause death in mice with serious infection. The recording was continued and five groups of experimental mice were included in the statistics. After the nasal dripping experiment, the body weight changes, the paralysis of the hind limbs of the mice, the smoothness of the hair of the mice and whether there were influenza-like symptoms were recorded.

Figure 9:
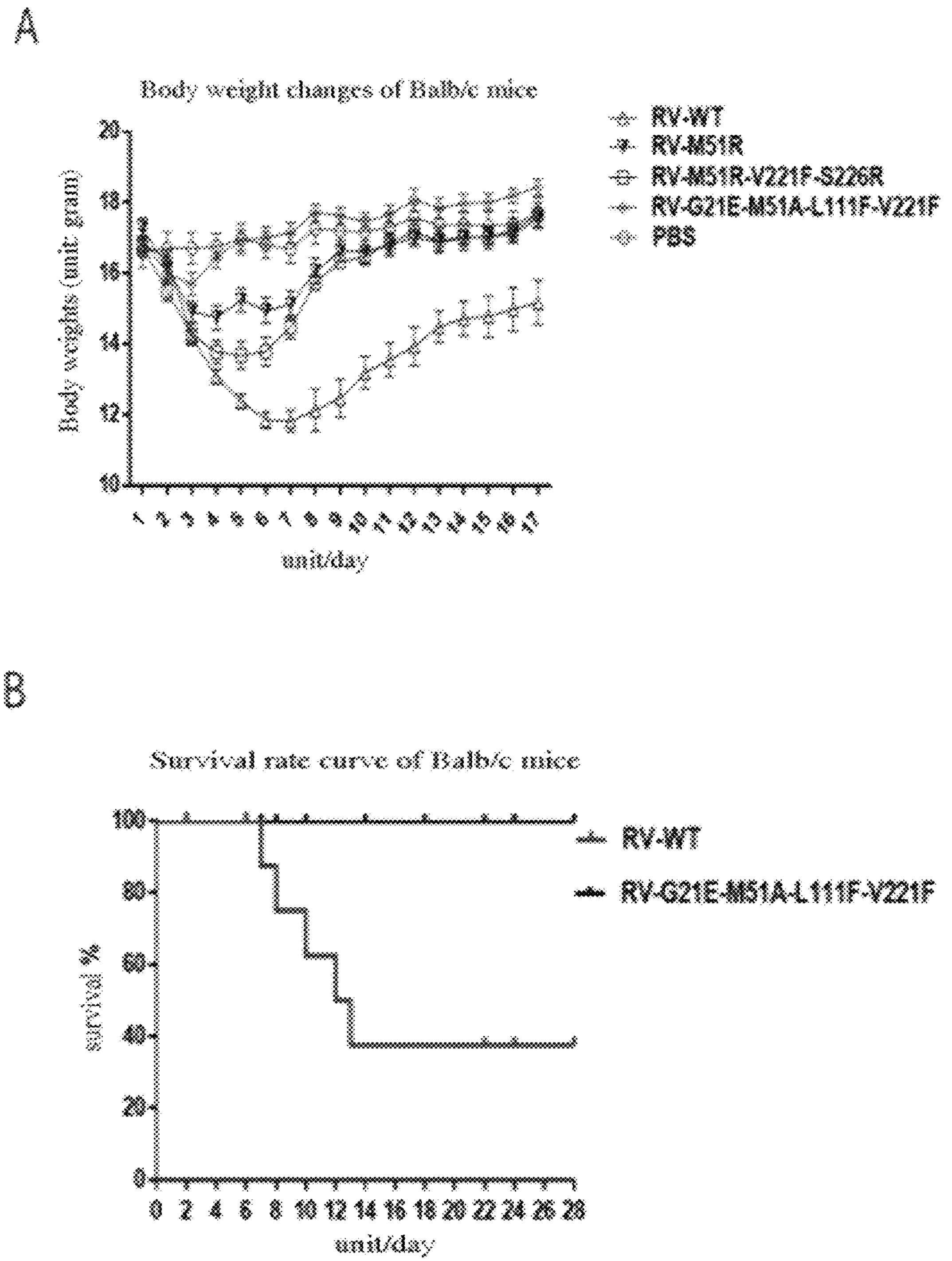
FIG. 9 shows the determination of neurotoxicity of different attenuated strains including RV-4Mut in different strains of mice.

The specific statistical results of the above experiment were as shown in Table 1 and FIG. 9.

TABLE 1

Verification of the neurotoxicity of RV-4Mut in animal models

| Groups of experiment | PBS | RV-GFP | RV-GFP-M51R | RV-GFP-M51R S226R-V221F | RV-GFP-G21E-M51R-L111F-V221F |
|---|---|---|---|---|---|
| Number of death | 0 | 6 | 0 | 0 | 0 |
| Mortality | 0% | 60% | 0% | 0% | 0% |
| Number of mild cases | 0 | 10 | 9 | 9 | 6 |
| Symptoms | None | Most serious, showing symptoms such as death, paralysis of hind limbs, messy hair, sneezing, and tail biting | Serious, showing symptoms such as paralysis of hind limbs, messy hair, and sneezing | Serious, showing symptoms such as paralysis of hind limbs and messy hair | Relatively mild, showing slightly fluffy and messy hair |
| Duration of symptoms | None | The longest duration (from the second day of nasal dripping to the end of the experiment) | Relatively long duration (6 days at most) | Relatively long duration (7 days at most) | Short duration (3 days at most) |
| Evaluation of recovery ability | Strongest (5*) | Weakest(1*) | Weak(2**) | Strong(3***) | Relatively strong (4****) |

As could be seen from Table 1 and FIG. 9, all 10 mice in VSV-WT nasal dripping group fell ill, meanwhile, the symptoms were severe, the conditions deteriorated rapidly, the final mortality reached 60% (as shown in FIG. 9B, 6 mice of the 10 mice inoculated with the wild-type virus strain died), the paralysis of the hind limbs occurred in all mice, and the symptoms lasted for a relatively long period of time. However, the mice infected with the other three attenuated strains had slightly reduced symptoms, especially only five mice in RV-4Mut nasal dripping group had mild symptoms, meanwhile, the mice in RV-4Mut group showed the fastest recovery. At the same time, the mice in RV-4Mut group showed no paralysis of the hind limbs and only had slightly messy hair. As shown in FIG. 9A, RV-4Mut group was the experimental group with the least significant weight loss, and the change trend of the body weights in RV-4Mut group was consistent with that in PBS nasal dripping group.

The above experimental results proved that the safety advantage of RV-4Mut attenuated strain in animal models was quite significant and excessive RV-4Mut did not exert any adverse effect on the survival of mice.

Example 8: Establishment of a Mouse Lung Cancer Model and Verification of the Efficacy of RV-4Mut Attenuated Strain Further, by establishing a mouse lung cancer model, the performances of the attenuated strain were tested via local intratumoral administration, so as to verify the efficacy of RV-4Mut attenuated strain.

The specific steps for establishing the above-mentioned mouse lung cancer model were as follows.

Each CB7BL/6 mouse was subcutaneously inoculated with $1.0\times10^6$ (200 μL) LLC-t2 cells. Tumor sizes were measured every other day, and tumor volumes were calculated according to the following formula: $\frac{1}{2}\times M2\times M1^2$ (M1:

short diameter, M2: long diameter). After the tumor volumes of the mice in each group exceeded 200 $mm^3$, the mice were administered with $10^6$ PFU (20 μl) of virus via intratumoral injection on Day 12, Day 14 and Day 16 for treatment, respectively. The tumor volume changes were continuously observed and recorded.

Figure 10:
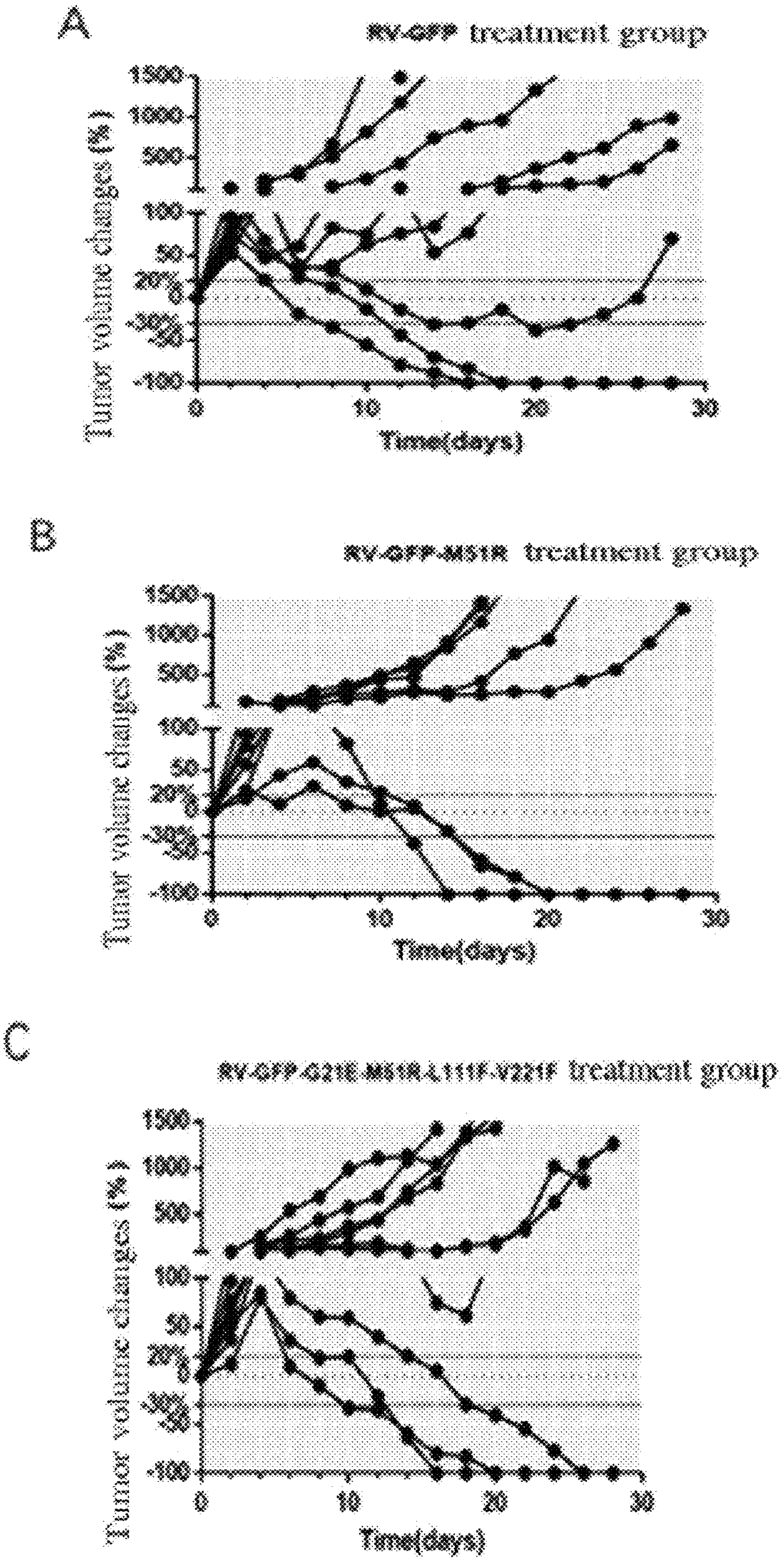
FIG. 10 shows the evaluation of the therapeutic effects of different attenuated strains including RV-4Mut in tumor models.
Figure 10:
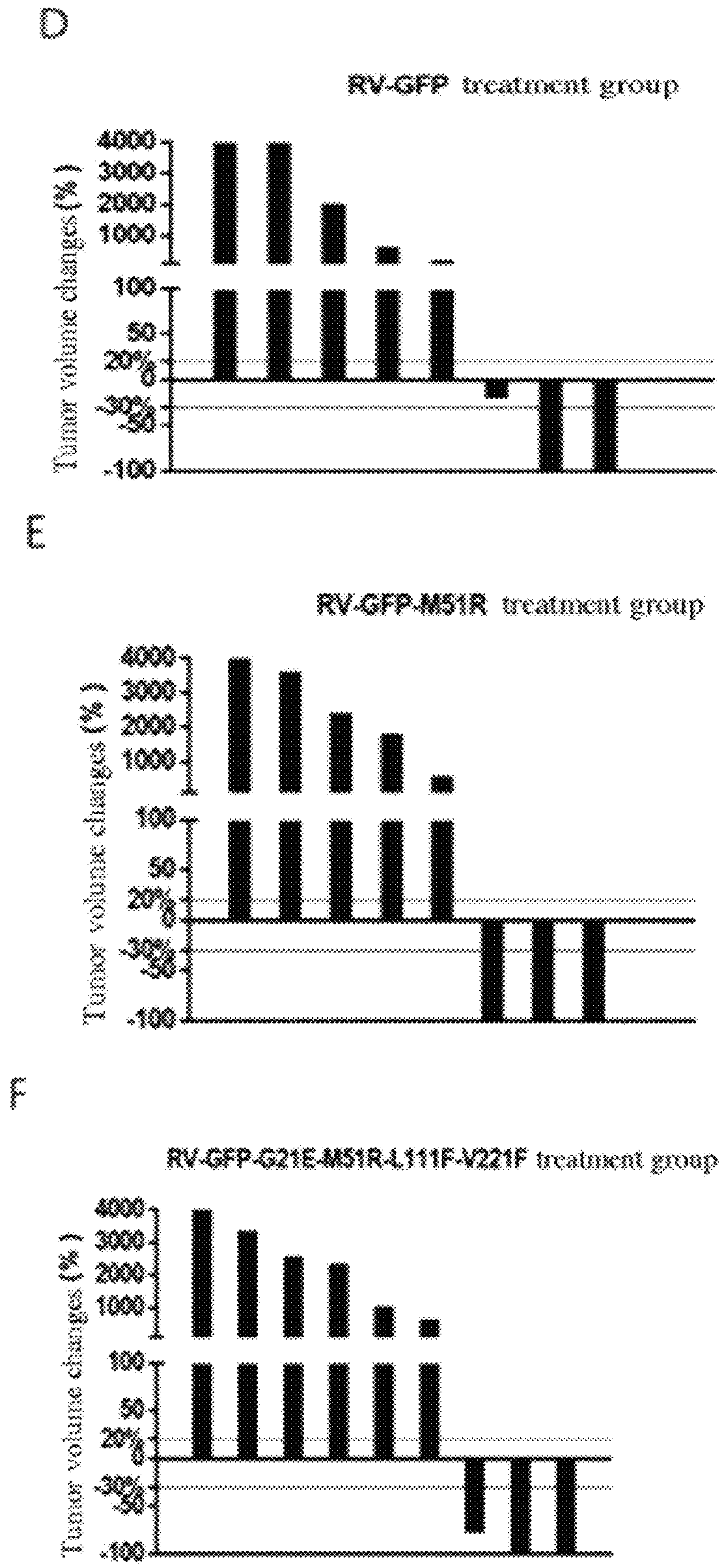

The results of the above experiment were as shown in FIG. 10.

As shown in FIG. 10C, the treatment of intratumorally injecting RV-4Mut every other day for three consecutive times was capable of effectively inhibiting the growth trend of tumors and greatly prolonging the lifespan of mice. By independently analyzing the therapeutic effects in each of the mice which respectively received three different attenuated strains, it was found that RV-4Mut and RV-GFP-M51R (control group) were both capable of reducing the tumor size until the tumor disappeared and achieving complete remission in 30% of the mice, and were capable of effectively inhibiting the tumor growth speed and achieving partial remission in approximately 40% of the mice.

As could be seen from FIG. 10, RV-4Mut immune treatment group had the least mice suffering from lung metastasis. By further recording the valid lifetime of the tumor-bearing mice that had received the treatment, it was found that the mice in the experimental group had the highest survival rate and approximately 40% of the mice maintained normal state of life within approximately two months (FIG. 10F), while the tumors of some tumor-bearing mice gradually regressed and these mice were completely cured, which further indicated that RV-4Mut attenuated strain showed significant therapeutic effects when administered to solid tumors and had good clinical application value.

The above-mentioned Examples of the present disclosure are merely exemplified to clearly illustrate the present disclosure rather than limitations to the embodiments of the present disclosure. For those of ordinary skill in the art, other changes or modifications in different forms may also be made based on the foregoing description. It is not necessary and impossible to enumerate all the embodiments. Any modification, equivalent replacement and improvement made within the spirits and principles of this disclosure shall be encompassed in the protection scope of the claims of the present disclosure.

What is claimed is:

1. A modified matrix protein (M) of a recombinant oncolytic rhabdovirus, wherein an amino acid sequence encoding the modified matrix protein (M) comprises a sequence which is at least 98% identical to an amino acid sequence as set forth in SEQ ID NO: 1; and wherein the sequence of the modified matrix protein (M) is the amino acid sequence encoding the modified matrix protein (M) and has the following mutations as compared with SEQ ID NO:1:

(i) mutation of glycine G to glutamic acid E at position 21, (ii) mutation of methionine M to alanine A at position 51, (iii) mutation of leucine L to phenylalanine F at position 111, and (iv) mutation of valine V to phenylalanine F at position 221.

2. The modified matrix protein (M) according to claim 1, wherein the recombinant oncolytic rhabdovirus is a vesicular stomatitis virus.

3. The modified matrix protein (M) according to claim 1, wherein the sequence of the modified matrix protein (M) is a sequence as set forth in SEQ ID NO:3.

4. A recombinant oncolytic rhabdovirus, wherein the recombinant oncolytic rhabdovirus generates a modified matrix protein (M), wherein an amino acid sequence of the modified matrix protein (M) is the amino acid sequence according to claim 1.

5. A composition comprising an isolated recombinant oncolytic rhabdovirus, wherein the recombinant oncolytic rhabdovirus comprises a nucleic acid fragment, the nucleic acid fragment encodes a modified matrix protein (M), wherein an amino acid sequence of the modified matrix protein (M) is the amino acid sequence according to claim 1.

6. The composition according to claim 5, wherein the composition further comprises a second oncolytic virus; wherein the second oncolytic virus is one or more selected from the group consisting of a rhabdovirus, a vaccinia virus, a herpes virus, a measles virus, a Newcastle disease virus, an adenovirus, an alphavirus, a parvovirus, and an enterovirus strain.

7. The composition according to claim 5, wherein the composition further comprises a second antitumor preparation; wherein the second antitumor preparation is an immunotherapeutic agent, a chemotherapeutic agent or a radiotherapeutic agent.

8. A vaccine, wherein the vaccine comprises a therapeutically effective amount of one or more recombinant oncolytic rhabdoviruses, wherein said one or more recombinant oncolytic rhabdoviruses comprise a modified matrix protein (M), and an amino acid sequence of the modified matrix protein (M) is the amino acid sequence according to claim 1.

9. The vaccine according to claim 8, wherein the vaccine may further comprise a second oncolytic virus or a second antitumor preparation.

10. An isolated peptide encoded by an amino acid sequence, wherein the amino acid sequence comprises a sequence which is at least 98% identical to an amino acid sequence of SEQ ID NO: 1;

wherein the amino acid sequence encoding the isolated peptide has the following mutations as compared with SEQ ID NO:1:

(i) mutation of glycine G to glutamic acid E at position 21, (ii) mutation of methionine M to alanine A at position 51, (iii) mutation of leucine L to phenylalanine F at position 111, and (iv) mutation of valine V to phenylalanine F at position 221.

11. A nucleotide sequence for encoding the isolated peptide according to claim 10.

12. A method for slowly and continuously killing abnormally proliferating cells, comprising a step of contacting the abnormally proliferating cells with a) a recombinant oncolytic rhabdovirus that generates a modified matrix protein (M) according to claim 1;

b) a composition comprising an isolated recombinant oncolytic rhabdovirus that comprises a nucleic acid fragment that encodes for said modified matrix protein (M); or c) a vaccine comprising a therapeutically effective amount of one or more said recombinant oncolytic rhabdoviruses comprising said modified matrix protein (M).

13. The method according to claim 12, wherein the abnormally proliferating cells are contained in the body of a patient.

14. The method according to claim 12, wherein the abnormally proliferating cells are tumor cells or tumor tissue-related cells.

15. The method according to claim 12, wherein the recombinant oncolytic rhabdovirus, the composition comprising the isolated recombinant oncolytic rhabdovirus, or the vaccine is administered to a patient.

16. The method according to claim 12, wherein the recombinant oncolytic rhabdovirus, the composition comprising the isolated recombinant oncolytic rhabdovirus, or the vaccine is administered via one or more administration modes selected from the group consisting of intraperitoneal administration, intravenous administration, intraarterial administration, intramuscular administration, intradermal administration, intratumoral administration, subcutaneous administration and intranasal administration.

17. The method according to claim 12 wherein the method further comprises a step of administering a second antitumor therapy.

18. The method according to claim 17, wherein the second antitumor therapy is administering a second oncolytic virus or the second antitumor therapy is one or more selected from the group consisting of chemotherapy, radiotherapy, immunotherapy and surgical therapy.

19. A method for inducing immune response in a subject, wherein the method comprises administering to a subject one or more selected from the group consisting of a) a recombinant oncolytic rhabdovirus that generates a modified matrix protein (M) according to claim 1;

b) a composition comprising an isolated recombinant oncolytic rhabdovirus that comprises a nucleic acid fragment that encodes for said modified matrix protein (M); and c) a vaccine comprising a therapeutically effective amount of one or more said recombinant oncolytic rhabdoviruses comprising said modified matrix protein (M).

20. A method for in ng and promoting antitumor immune response or eliminating immunosuppression in a microenvironment of a tumor tissue comprising a step of contacting a tumor or a tumor tissue with a) recombinant oncolytic rhabdovirus that generates a modified matrix protein (M) according to claim 1;

b) a composition comprising an isolated recombinant oncolytic rhabdovirus that comprises a nucleic acid fragment that encodes for said modified matrix protein (M); or c) a vaccine comprising a therapeutically effective amount of one or more said recombinant oncolytic rhabdoviruses comprising said modified matrix protein (M).

21. The isolated peptide according to claim 10, wherein the amino acid sequence is a sequence as set forth in SEQ ID NO: 3.

22. The method of claim 12, wherein a) said recombinant oncolytic rhabdovirus is an attenuated virus; b) the vaccine further comprises a second oncolytic agent; c) the vaccine further comprises a second antitumor preparation; and/or d) the method further comprises 1) administering a second oncolytic virus selected from the group consisting of rhabdovirus, vaccinia virus, herpes virus, measles virus, Newcastle disease virus, adenovirus, alphavirus, parvovirus, enterovirus strain, attenuated oncolytic virus, and attenuated rhabdovirus; or 2) administering a second antitumor preparation selected from the group consisting of immunotherapeutic agent, chemotherapeutic agent, radiotherapeutic agent, small molecule, macromolecule, cell, viral vector, gene vector, DNA, RNA, polypeptide and nanocomposite.

23. The method of claim 14, wherein the tumor cells are selected from the group consisting of cancer cells and metastatic cancer cells.

24. The method of claim 16, wherein the administration mode is one or more of endoscopy, celioscopy, intervention, minimal invasive surgery, or traditional surgery.

25. The method of claim 18, wherein the second oncolytic virus is one or more of a rhabdovirus, a vaccinia virus, a herpes virus, a measles virus, a Newcastle disease virus, an adenovirus, an alphavirus, a parvovirus, or an enterovirus strain.

26. The method of claim 25, wherein the second oncolytic virus is selected from the group consisting of an attenuated oncolytic virus and an attenuated rhabdovirus.

27. The method of claim 19, wherein a) said recombinant oncolytic rhabdovirus is an attenuated virus; b) the vaccine further comprises a second oncolytic agent; c) the vaccine further comprises a second antitumor preparation; and/or d) the method further comprises 1) administering a second oncolytic virus selected from the group consisting of rhabdovirus, vaccinia virus, herpes virus, measles virus, Newcastle disease virus, adenovirus, alphavirus, parvovirus, enterovirus strain, attenuated oncolytic virus, and attenuated rhabdovirus; or 2) administering a second antitumor preparation selected from the group consisting of immunotherapeutic agent, chemotherapeutic agent, radiotherapeutic agent, small molecule, macromolecule, cell, viral vector, gene vector, DNA, RNA, polypeptide and nanocomposite.

28. The method of claim 20, wherein a) said recombinant oncolytic rhabdovirus is an attenuated virus; b) the vaccine further comprises a second oncolytic agent; c) the vaccine further comprises a second antitumor preparation; and/or d) the method further comprises 1) administering a second oncolytic virus selected from the group consisting of rhabdovirus, vaccinia virus, herpes virus, measles virus, Newcastle disease virus, adenovirus, alphavirus, parvovirus, enterovirus strain, attenuated oncolytic virus, and attenuated rhabdovirus; or 2) administering a second antitumor preparation selected from the group consisting of immunotherapeutic agent, chemotherapeutic agent, radiotherapeutic agent, small molecule, macromolecule, cell, viral vector, gene vector, DNA, RNA, polypeptide and nanocomposite.

* * * * *

```
                    SEQUENCE LISTING

<160> NUMBER OF SEQ ID NOS: 4

<210> SEQ ID NO 1
<211> LENGTH: 229
<212> TYPE: PRT
<213> ORGANISM: Vesicular stomatitis virus

<400> SEQUENCE: 1

Met Ser Ser Leu Lys Lys Ile Leu Gly Leu Lys Gly Lys Gly Lys Lys
1               5                   10                  15

Ser Lys Lys Leu Gly Ile Ala Pro Pro Pro Tyr Glu Glu Asp Thr Ser
            20                  25                  30

Met Glu Tyr Ala Pro Ser Ala Pro Ile Asp Lys Ser Tyr Phe Gly Val
        35                  40                  45

Asp Glu Met Asp Thr Tyr Asp Pro Asn Gln Leu Arg Tyr Glu Lys Phe
    50                  55                  60

Phe Phe Thr Val Lys Met Thr Val Arg Ser Asn Arg Pro Phe Arg Thr
65                  70                  75                  80

Tyr Ser Asp Val Ala Ala Ala Val Ser His Trp Asp His Met Tyr Ile
                85                  90                  95

Gly Met Ala Gly Lys Arg Pro Phe Tyr Lys Ile Leu Ala Phe Leu Gly
            100                 105                 110

Ser Ser Asn Leu Lys Ala Thr Pro Ala Val Leu Ala Asp Gln Gly Gln
        115                 120                 125

Pro Glu Tyr His Ala His Cys Glu Gly Arg Ala Tyr Leu Pro His Arg
    130                 135                 140

Met Gly Lys Thr Pro Pro Met Leu Asn Val Pro Glu His Phe Arg Arg
145                 150                 155                 160

Pro Phe Asn Ile Gly Leu Tyr Lys Gly Thr Ile Glu Leu Thr Met Thr
                165                 170                 175

Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Val Leu Asp Ser
    210                 215                 220
```

-continued

Ile Gly His Phe Lys
225

<210> SEQ ID NO 2
<211> LENGTH: 690
<212> TYPE: DNA
<213> ORGANISM: Vesicular stomatitis virus

<400> SEQUENCE: 2
atgagttcct taaagaagat tctcggtctg aaggggaaag gtaagaaatc taagaaatta 60
gggatcgcac cacccccta tgaagaggac actagcatgg agtatgctcc gagcgctcca 120
attgacaaat cctattttgg agttgacgag atggacacct atgatccgaa tcaattaaga 180
tatgagaaat tcttctttac agtgaaaatg acggttagat ctaatcgtcc gttcagaaca 240
tactcagatg tggcagccgc tgtatcccat tgggatcaca tgtacatcgg aatggcaggg 300
aaacgtccct tctacaaaat cttggctttt ttgggttctt ctaatctaaa ggccactcca 360
gcggtattgg cagatcaagg tcaaccagag tatcacgctc actgcgaagg cagggcttat 420
ttgccacata ggatggggaa gacccctccc atgctcaatg taccagagca cttcagaaga 480
ccattcaata taggtcttta caagggaacg attgagctca caatgaccat ctacgatgat 540
gagtcactgg aagcagctcc tatgatctgg gatcatttca attcttccaa attttctgat 600
ttcagagaga aggccttaat gtttggcctg attgtcgaga aaaaggcatc tggagcgtgg 660
gtcctggact ctatcggcca cttcaaatga 690

<210> SEQ ID NO 3
<211> LENGTH: 229
<212> TYPE: PRT
<213> ORGANISM: Artificial Sequence
<220> FEATURE:
<223> OTHER INFORMATION: The amino acid sequence of the modified matrix protein (M)

<400> SEQUENCE: 3

Met Ser Ser Leu Lys Lys Ile Leu Gly Leu Lys Gly Lys Gly Lys Lys
1 5 10 15

Ser Lys Lys Leu Glu Ile Ala Pro Pro Pro Tyr Glu Glu Asp Thr Ser
20 25 30

Met Glu Tyr Ala Pro Ser Ala Pro Ile Asp Lys Ser Tyr Phe Gly Val
35 40 45

Asp Glu Ala Asp Thr Tyr Asp Pro Asn Gln Leu Arg Tyr Glu Lys Phe
50 55 60

Phe Phe Thr Val Lys Met Thr Val Arg Ser Asn Arg Pro Phe Arg Thr
65 70 75 80

Tyr Ser Asp Val Ala Ala Ala Val Ser His Trp Asp His Met Tyr Ile
85 90 95

Gly Met Ala Gly Lys Arg Pro Phe Tyr Lys Ile Leu Ala Phe Phe Gly
100 105 110

Ser Ser Asn Leu Lys Ala Thr Pro Ala Val Leu Ala Asp Gln Gly Gln
115 120 125

Pro Glu Tyr His Ala His Cys Glu Gly Arg Ala Tyr Leu Pro His Arg
130 135 140

Met Gly Lys Thr Pro Pro Met Leu Asn Val Pro Glu His Phe Arg Arg
145 150 155 160

Pro Phe Asn Ile Gly Leu Tyr Lys Gly Thr Ile Glu Leu Thr Met Thr
165 170 175

-continued

```
Ile Tyr Asp Asp Glu Ser Leu Glu Ala Ala Pro Met Ile Trp Asp His
            180                 185                 190

Phe Asn Ser Ser Lys Phe Ser Asp Phe Arg Glu Lys Ala Leu Met Phe
        195                 200                 205

Gly Leu Ile Val Glu Lys Lys Ala Ser Gly Ala Trp Phe Leu Asp Ser
    210                 215                 220

Ile Gly His Phe Lys
225


<210> SEQ ID NO 4
<211> LENGTH: 690
<212> TYPE: DNA
<213> ORGANISM: Artificial Sequence
<220> FEATURE:
<223> OTHER INFORMATION: The nucleotide sequence of the modified matrix
      protein (M)

<400> SEQUENCE: 4

atgagttcct taaagaagat tctcggtctg aaggggaaag gtaagaaatc taagaaatta     60

gagatcgcac cacccccta tgaagaggac actagcatgg agtatgctcc gagcgctcca     120

attgacaaat cctattttgg agttgacgag gcggacacct atgatccgaa tcaattaaga    180

tatgagaaat tcttctttac agtgaaaatg acggttagat ctaatcgtcc gttcagaaca    240

tactcagatg tggcagccgc tgtatcccat tgggatcaca tgtacatcgg aatggcaggg    300

aaacgtccct tctacaaaat cttggctttc ttcggttctt ctaatctaaa ggccactcca    360

gcggtattgg cagatcaagg tcaaccagag tatcacgctc actgcgaagg cagggcttat    420

ttgccacata ggatggggaa gacccctccc atgctcaatg taccagagca cttcagaaga    480

ccattcaata taggtcttta caagggaacg attgagctca caatgaccat ctacgatgat    540

gagtcactgg aagcagctcc tatgatctgg gatcatttca attcttccaa attttctgat    600

ttcagagaga aggccttaat gtttggcctg attgtcgaga aaaaggcatc tggagcgtgg    660

ttcctggact ctatcggcca cttcaaatga                                      690
```